United States Patent
Yoshida et al.

(10) Patent No.: US 12,397,175 B2
(45) Date of Patent: Aug. 26, 2025

(54) RADIATION TREATMENT SYSTEM AND METHOD OF OPERATING RADIATION TREATMENT SYSTEM

(71) Applicant: Hitachi High-Tech Corporation, Tokyo (JP)

(72) Inventors: Mitsuhiro Yoshida, Tokyo (JP); Yojiro Kobayashi, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 199 days.

(21) Appl. No.: 17/942,298

(22) Filed: Sep. 12, 2022

(65) Prior Publication Data
US 2023/0101051 A1   Mar. 30, 2023

(30) Foreign Application Priority Data
Sep. 29, 2021   (JP) .................................. 2021-159910

(51) Int. Cl.
*A61N 5/10*   (2006.01)

(52) U.S. Cl.
CPC ......... *A61N 5/1071* (2013.01); *A61N 5/1045* (2013.01); *A61N 5/1081* (2013.01); *A61N 2005/1092* (2013.01)

(58) Field of Classification Search
None
See application file for complete search history.

(56) References Cited

U.S. PATENT DOCUMENTS

| | | | | |
|---|---|---|---|---|
| 6,853,703 B2 * | 2/2005 | Svatos | ................ | A61N 5/1042 378/65 |
| 7,166,852 B2 * | 1/2007 | Saracen | ............... | A61N 5/1049 250/491.1 |
| 7,298,385 B2 * | 11/2007 | Kazi | ..................... | B25J 9/1671 700/254 |

(Continued)

FOREIGN PATENT DOCUMENTS

| | | |
|---|---|---|
| JP | 2008-173182 A | 7/2008 |
| JP | 2015-100455 A | 6/2015 |
| JP | 2020-528780 A | 10/2020 |

OTHER PUBLICATIONS

Extended European Search Report received in corresponding European Application No. 22196451.3 dated Feb. 23, 2023.

(Continued)

*Primary Examiner* — David P Porta
*Assistant Examiner* — Djura Malevic
(74) *Attorney, Agent, or Firm* — Mattingly & Malur, PC

(57) ABSTRACT

To provide a radiation treatment system which enables wide irradiation range of radiation to a patient without increasing a load on a structure body. A radiation treatment system includes: a couch that carries a treatment target; a radiation source; a rotation mechanism configured to support the radiation source and to rotate the radiation source around the couch; a sensor configured to detect radiation transmitted through the treatment target; and a control unit configured to control the radiation source and the rotation mechanism, and the control unit sets an irradiation plan in which an irradiation range of first irradiation and an irradiation range of second irradiation are partially overlapped, and controls a radiation dose for an overlapping portion based on a detection result obtained by the sensor.

7 Claims, 23 Drawing Sheets

(56) References Cited

U.S. PATENT DOCUMENTS

| | | | | |
|---|---|---|---|---|
| 7,525,104 B2* | 4/2009 | Harada | G21K 5/04 | 250/503.1 |
| 7,695,192 B2* | 4/2010 | Henderson | A61B 6/4458 | 378/198 |
| 7,784,127 B2* | 8/2010 | Kuro | A61B 6/465 | 5/616 |
| 7,875,861 B2* | 1/2011 | Huttenberger | A61N 5/1049 | 5/601 |
| 7,957,508 B2* | 6/2011 | Brooks | A61B 6/4258 | 378/65 |
| 8,002,465 B2* | 8/2011 | Ahn | A61N 5/1049 | 378/65 |
| 8,319,198 B2* | 11/2012 | Bert | A61N 5/1043 | 250/492.3 |
| 8,502,177 B2* | 8/2013 | Bert | A61N 5/10 | 378/65 |
| 8,575,563 B2* | 11/2013 | Cameron | A61N 5/1077 | 250/397 |
| 8,625,739 B2* | 1/2014 | Balakin | A61N 5/00 | 378/65 |
| 8,653,473 B2* | 2/2014 | Yajima | A61N 5/1081 | 250/492.1 |
| 8,791,656 B1* | 7/2014 | Zwart | H05H 13/02 | 315/501 |
| 8,975,836 B2* | 3/2015 | Bromberg | H01F 6/06 | 315/502 |
| 9,326,907 B2* | 5/2016 | Marle | A61B 6/0407 | |
| 9,795,361 B2* | 10/2017 | Marx | B25J 9/1679 | |
| 9,833,897 B2* | 12/2017 | SøE-Knudsen | B25J 9/1682 | |
| 9,844,871 B2* | 12/2017 | Goodwin | B25J 9/06 | |
| 9,986,960 B2* | 6/2018 | Ay | A61B 6/037 | |
| 10,188,356 B2* | 1/2019 | Guertin | A61B 6/4441 | |
| 10,265,544 B2* | 4/2019 | Bharat | A61B 5/0261 | |
| 10,293,186 B2* | 5/2019 | Sun | A61N 5/1049 | |
| 10,463,881 B2* | 11/2019 | Gerbershagen | H05H 7/04 | |
| 10,485,995 B2* | 11/2019 | Anferov | A61N 5/1077 | |
| 10,603,518 B2* | 3/2020 | Hassan | H05H 7/001 | |
| 10,675,487 B2* | 6/2020 | Zwart | G21K 1/10 | |
| 10,688,659 B2* | 6/2020 | Gomi | B25J 18/00 | |
| 10,702,715 B2* | 7/2020 | Pearce | A61N 5/1075 | |
| 10,806,409 B2* | 10/2020 | Kruesi | A61B 6/0407 | |
| 10,806,950 B2* | 10/2020 | Fahrig | A61N 5/1078 | |
| 10,813,816 B2* | 10/2020 | Yano | A61B 6/055 | |
| 11,013,937 B2* | 5/2021 | Kumar | A61N 5/1077 | |
| 11,103,730 B2* | 8/2021 | Zwart | A61N 5/1069 | |
| 11,247,073 B2* | 2/2022 | Nagamoto | A61B 6/0487 | |
| 11,369,806 B2* | 6/2022 | Laurence, Jr. | A61N 5/1081 | |
| 11,389,669 B2* | 7/2022 | Traneus | A61N 5/1081 | |
| 11,504,550 B2* | 11/2022 | Maolinbay | A61N 5/1067 | |
| 11,521,820 B2* | 12/2022 | Fishman | H01J 35/153 | |
| 11,672,491 B2* | 6/2023 | Fishman | A61B 6/4458 | 600/3 |
| 11,697,031 B2* | 7/2023 | Kaneko | A61N 5/1081 | 378/65 |
| 11,794,036 B2* | 10/2023 | Bassalow | A61N 5/1075 | |
| 2003/0048875 A1* | 3/2003 | Mihara | A61N 5/10 | 378/196 |
| 2004/0172756 A1* | 9/2004 | Somasundaram | A61B 6/0487 | 5/601 |
| 2004/0213381 A1* | 10/2004 | Harada | G21K 1/046 | 378/152 |
| 2005/0085710 A1* | 4/2005 | Earnst | A61B 6/0487 | 378/65 |
| 2005/0226377 A1* | 10/2005 | Wong | G05B 19/4061 | 378/65 |
| 2005/0228255 A1* | 10/2005 | Saracen | A61B 6/548 | 600/407 |
| 2005/0234327 A1* | 10/2005 | Saracen | A61B 6/548 | 600/407 |
| 2006/0106301 A1* | 5/2006 | Kats | A61N 5/1078 | 600/415 |
| 2007/0051904 A1* | 3/2007 | Kaiser | A61N 5/10 | 250/492.1 |
| 2008/0093567 A1* | 4/2008 | Gall | H05H 13/02 | 250/493.1 |
| 2008/0170663 A1* | 7/2008 | Urano | A61N 5/1049 | 378/65 |
| 2008/0219407 A1* | 9/2008 | Kaiser | A61N 5/1081 | 378/65 |
| 2009/0065717 A1* | 3/2009 | Kaiser | A61N 5/1049 | 250/505.1 |
| 2010/0090122 A1* | 4/2010 | Balakin | A61N 5/10 | 250/424 |
| 2011/0085640 A1* | 4/2011 | Fadler | A61B 6/4441 | 378/65 |
| 2011/0124976 A1* | 5/2011 | Sabczynski | G16H 30/20 | 703/11 |
| 2011/0272600 A1* | 11/2011 | Bert | A61N 5/103 | 250/492.1 |
| 2011/0301449 A1* | 12/2011 | Maurer, Jr. | A61B 6/032 | 378/65 |
| 2012/0001085 A1* | 1/2012 | Fujimoto | A61N 5/1043 | 250/396 ML |
| 2012/0307973 A1* | 12/2012 | Dirauf | A61N 5/1049 | 378/62 |
| 2013/0187060 A1* | 7/2013 | Jongen | H01J 3/26 | 250/396 R |
| 2013/0208867 A1* | 8/2013 | Beckman | A61N 5/1084 | 378/65 |
| 2013/0217946 A1* | 8/2013 | Balakin | H05H 7/10 | 600/1 |
| 2013/0256551 A1* | 10/2013 | Yao | A61N 5/1082 | 250/393 |
| 2014/0094638 A1* | 4/2014 | Gall | A61N 5/1077 | 315/502 |
| 2014/0371511 A1* | 12/2014 | Zwart | A61N 5/1077 | 315/502 |
| 2015/0146856 A1* | 5/2015 | Beckman | A61N 5/1084 | 378/65 |
| 2015/0182175 A1* | 7/2015 | Handa | A61B 6/4085 | 378/9 |
| 2016/0067525 A1* | 3/2016 | Bouchet | A61N 5/1069 | 600/1 |
| 2016/0247591 A1* | 8/2016 | Bromberg | A61N 5/1077 | |
| 2017/0128746 A1* | 5/2017 | Zwart | A61N 5/1077 | |
| 2017/0157426 A1* | 6/2017 | Buchsbaum | A61N 5/1067 | |
| 2018/0064958 A1* | 3/2018 | Kobayashi | A61N 5/1081 | |
| 2018/0133508 A1* | 5/2018 | Pearce | A61N 5/107 | |
| 2018/0236268 A1* | 8/2018 | Zwart | A61N 5/1081 | |
| 2019/0054320 A1 | 2/2019 | Owens et al. | | |
| 2019/0204146 A1* | 7/2019 | Wei | G01J 1/0209 | |
| 2019/0308034 A1* | 10/2019 | Nagamoto | A61B 6/50 | |
| 2020/0002980 A1* | 1/2020 | Ketels | E05B 83/30 | |
| 2020/0298025 A1* | 9/2020 | Cooley, III | A61N 5/1031 | |
| 2021/0077828 A1* | 3/2021 | Wang | A61N 5/1049 | |
| 2021/0162236 A1* | 6/2021 | Shvartsman | G01R 33/3806 | |
| 2021/0187328 A1* | 6/2021 | Bottura | A61N 5/1077 | |
| 2021/0290979 A1* | 9/2021 | Liu | A61N 5/1065 | |
| 2021/0299473 A1* | 9/2021 | Kaneko | A61N 5/1082 | |
| 2022/0126117 A1* | 4/2022 | Voronenko | A61N 5/1031 | |
| 2022/0249872 A1* | 8/2022 | Seco | A61N 5/1081 | |
| 2022/0305292 A1* | 9/2022 | Harper | A61N 5/1084 | |
| 2022/0347494 A1* | 11/2022 | Debatty | A61N 5/1049 | |
| 2023/0101051 A1* | 3/2023 | Yoshida | A61N 5/1082 | 600/1 |
| 2025/0128092 A1* | 4/2025 | Angerud | A61N 5/1031 | |

OTHER PUBLICATIONS

Japanese Office Action received in corresponding Japanese Application No. 2021-159910 dated Sep. 17, 2024.

* cited by examiner

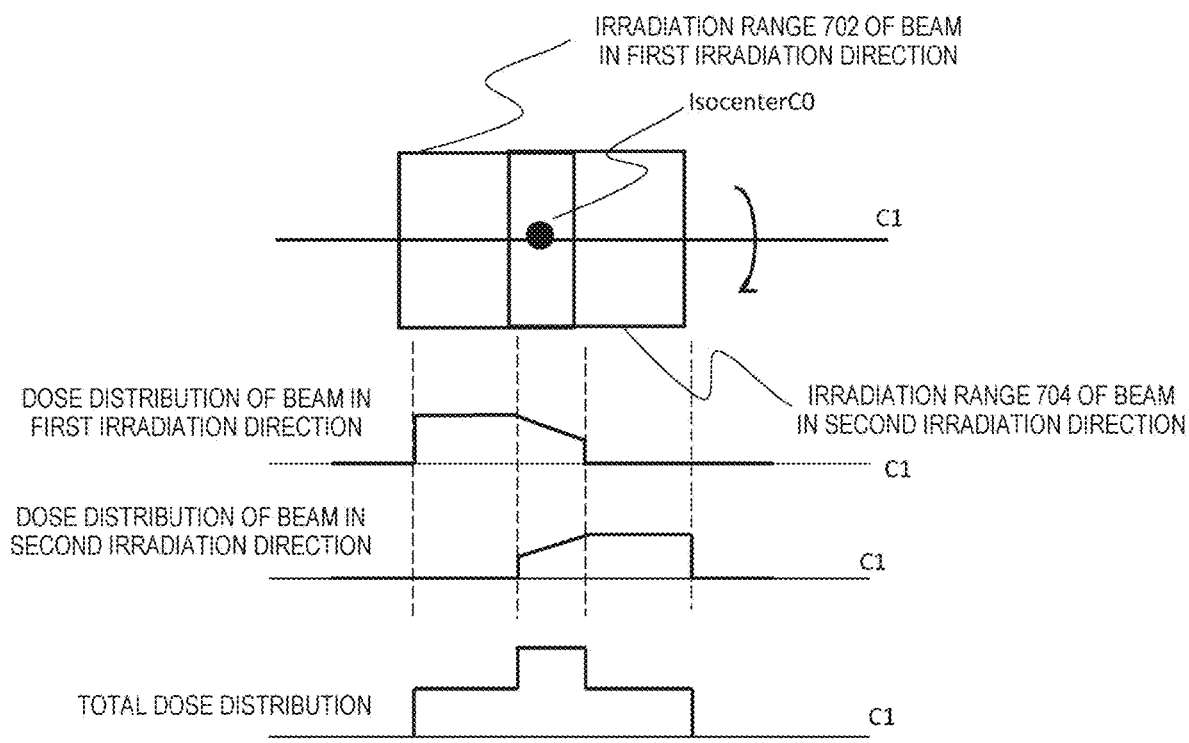

FIG. 21

| TREATMENT PLAN | IRRADIATION CONTROL |
|---|---|
| THERE IS SCHEDULE OF NEXT IRRADIATION TREATMENT WITHIN PREDETERMINED NUMBER OF DAYS. | CORRECT SECOND TIME OF RADIATION DOSE BASED ON FIRST TIME OF DOSE DISTRIBUTION, AND ADJUST TOTAL OF TWO DOSES TO TARGET DOSE. REFLECT EXCESS OR DEFICIENCY IN NEXT TREATMENT. |
| THERE IS NO SCHEDULE OF NEXT IRRADIATION TREATMENT WITHIN PREDETERMINED NUMBER OF DAYS. | SET FIRST AND SECOND TIMES OF RADIATION DOSES TO BE SMALL, AND ADJUST RADIATION DOSE TO TARGET DOSE IN ADDITIONAL IRRADIATION. |

RADIATION TREATMENT SYSTEM AND METHOD OF OPERATING RADIATION TREATMENT SYSTEM

CROSS-REFERENCE TO RELATED APPLICATION

The present application claims priority from Japanese application JP2021-159910, filed on Sep. 29, 2021, the contents of which is hereby incorporated by reference into this application.

BACKGROUND OF THE INVENTION

1. Field of the Invention

The present invention relates to a radiation treatment system and a method of operating a radiation treatment system.

2. Description of the Related Art

A radiation treatment method includes a method of using a linear accelerator called a linac as a radiation source, and emitting radiation to an affected part of a patient, which is previously imaged with an X-ray CT apparatus, an MRI apparatus, or the like, from various directions in three dimensions.

For example, an intensity modulated radiation treatment (IMRT) method of shielding a part of a radiation beam emitted from the radiation source by using a multi-leaf collimator (MLC) and irradiating the affected part while modulating a radiation intensity distribution of a region irradiated with the radiation, and a volumetric modulated arc therapy (VMAT) in which the multi-leaf collimator and the radiation are rotated around the patient at that time are known.

In addition, an image-guided radiotherapy (IGRT) method in which a radiation treatment apparatus equipped with an X-ray imaging apparatus is used to take an X-ray image immediately before the irradiation with the radiation, and the image is compared with the image taken in advance, thus adjusting an X-ray irradiation position that is determined based on the image taken in advance is also known.

A moving object tracking irradiation method is also known in which when the affected part moves due to a respiratory motion, or the like, a position of the affected part is obtained based on the image taken by the X-ray imaging apparatus, a direction of the radiation source is tilted by a gimbal mechanism, and a radiation irradiation direction is made to follow the position of the affected part.

A tomotherapy method is also known in which the volumetric modulated arc therapy (rotation IMRT) and the image-guided radiotherapy (IGRT) are combined, and further helical irradiation is performed while moving a couch on which the patient is placed.

Also, in order to widen a radiation irradiation range on the patient, JP-A-2008-173182 proposes a method of sequentially performing irradiation with fan beams in adjacent irradiation ranges by tilting a radiation axis from a radiation source at the same position. Further, JP-A-2015-100455 proposes a method of widening the radiation irradiation range by moving an irradiation region by changing a direction of a radiation source while emitting the radiation.

In a radiation treatment, it is required to widen a range in which the irradiation with radiation can be performed and to control an irradiation amount of the radiation with high accuracy.

As in JP-A-2008-173182, when the irradiation is sequentially performed in the adjacent irradiation ranges, the irradiation can be performed in a wide range, but a gap region or an overlapping region is generated between the irradiation ranges, and an excess or deficiency of an irradiation amount of these regions is generated.

In addition, as in JP-A-2015-100455, when the irradiation is performed while changing a direction of an irradiation axis of a radiation apparatus with respect to a rotation axis of the radiation apparatus, a demand for control of the irradiation axis and the MLC at an overlapping region or an irradiation end portion is severe, and it is difficult to control the irradiation amount with high accuracy.

SUMMARY OF THE INVENTION

An object of the invention is to provide a radiation treatment system capable of performing irradiation in a wide range with high accuracy.

In order to achieve the above object, a radiation treatment system of the invention includes: a couch that carries a treatment target; a radiation source; a rotation mechanism configured to support the radiation source and to rotate the radiation source around the couch; a sensor configured to detect radiation transmitted through the treatment target; and a control unit configured to control the radiation source and the rotation mechanism, and the control unit sets an irradiation plan in which an irradiation range of first irradiation and an irradiation range of second irradiation are partially overlapped, and controls a radiation dose for an overlapping portion based on a detection result obtained by the sensor.

According to one method of operating a radiation treatment system of the invention, the radiation treatment system includes: a couch on which a treatment target is placed; a radiation source; a rotation mechanism configured to support the radiation source and to rotate the radiation source around the couch; a sensor configured to detect radiation transmitted through the treatment target; and a control unit configured to control the radiation source and the rotation mechanism, and the method of operating a radiation treatment system executed by the control unit includes: a step of setting an irradiation plan in which an irradiation range of first irradiation and an irradiation range of second irradiation are partially overlapped, a step of acquiring a detection result by the sensor while executing at least the first irradiation, a step of, based on the detection result, performing correction of a radiation dose emitted to an overlapping portion in subsequent irradiation, and a step of performing irradiation reflecting the correction.

According to the invention, the radiation treatment system enables wide range irradiation with high accuracy.

BRIEF DESCRIPTION OF THE DRAWINGS

FIGS. 8A-1 and 8A-2 are diagrams showing first and second irradiation directions and irradiation ranges in the radiation irradiation apparatus of the embodiment, and FIGS. 8B-1 and 8B-2 are diagrams showing an irradiation direction and an irradiation range of a comparative example.

FIG. 10 is a diagram showing the dose distributions based on irradiation with the beams in the first and second irradiation directions of the radiation irradiation apparatus of the embodiment and the total dose distribution thereof.

FIG. 21 is a diagram illustrating irradiation control according to a treatment plan.

DESCRIPTION OF THE PREFERRED EMBODIMENTS

A radiation treatment system according to one embodiment of the invention will be described.

Apparatus Configuration of Radiation treatment System

First, an apparatus configuration of the radiation treatment system of the present embodiment will be described.

Figure 1:
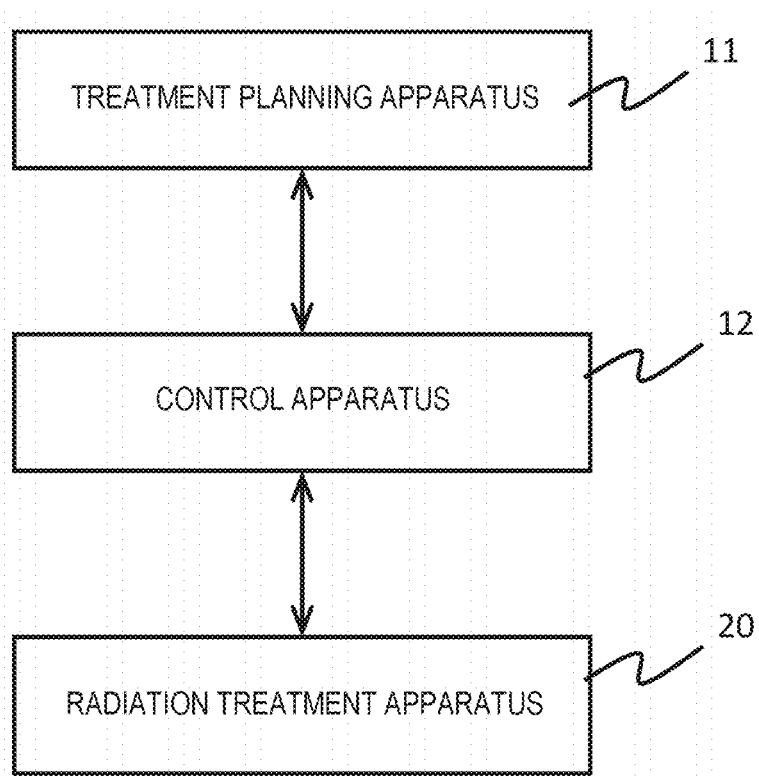
FIG. 1 is a block diagram of a radiation treatment system according to an embodiment of the invention.

As shown in FIG. 1, a radiation treatment system 10 includes a treatment planning apparatus 11, a control apparatus (control unit) 12, and a radiation treatment apparatus 20.

The treatment planning apparatus 11 receives three-dimensional image data captured in advance for a patient B as a treatment target, and creates, as a treatment plan, properties of radiation to be emitted to the patient B (a dose, a time, an angle, a position, a radiation region, and the like of the radiation to be emitted to the patient B) according to contents of a radiation treatment. Further, in order to emit the radiation with the dose, the time, the angle, and the like of the radiation of the treatment plan, the treatment planning apparatus 11 outputs, to the control apparatus 12, control parameter values such as a tilt angle of a head swing mechanism 301 of a radiation source to be described later, a rotation angle of a rotation ring 22 with respect to a ring frame 21, and an irradiation timing of a rotation shaft 25 and a radiation irradiation apparatus 24 as an irradiation plan. A long-term plan can be made as the treatment plan. In the long-term plan, an entire treatment plan is implemented by a combination of a schedule and an individual treatment plan, such as a day of a first time of irradiation treatment and the treatment plan thereof, a day of a second time of irradiation treatment and the treatment plan thereof.

The control apparatus 12 controls an operation of the radiation treatment apparatus 20 based on the control parameter values (irradiation plan) received from the treatment planning apparatus 11. The control apparatus 12 includes a CPU and a memory, and the CPU reads and executes a program stored in the memory in advance to execute a control operation by software.

Figure 2:
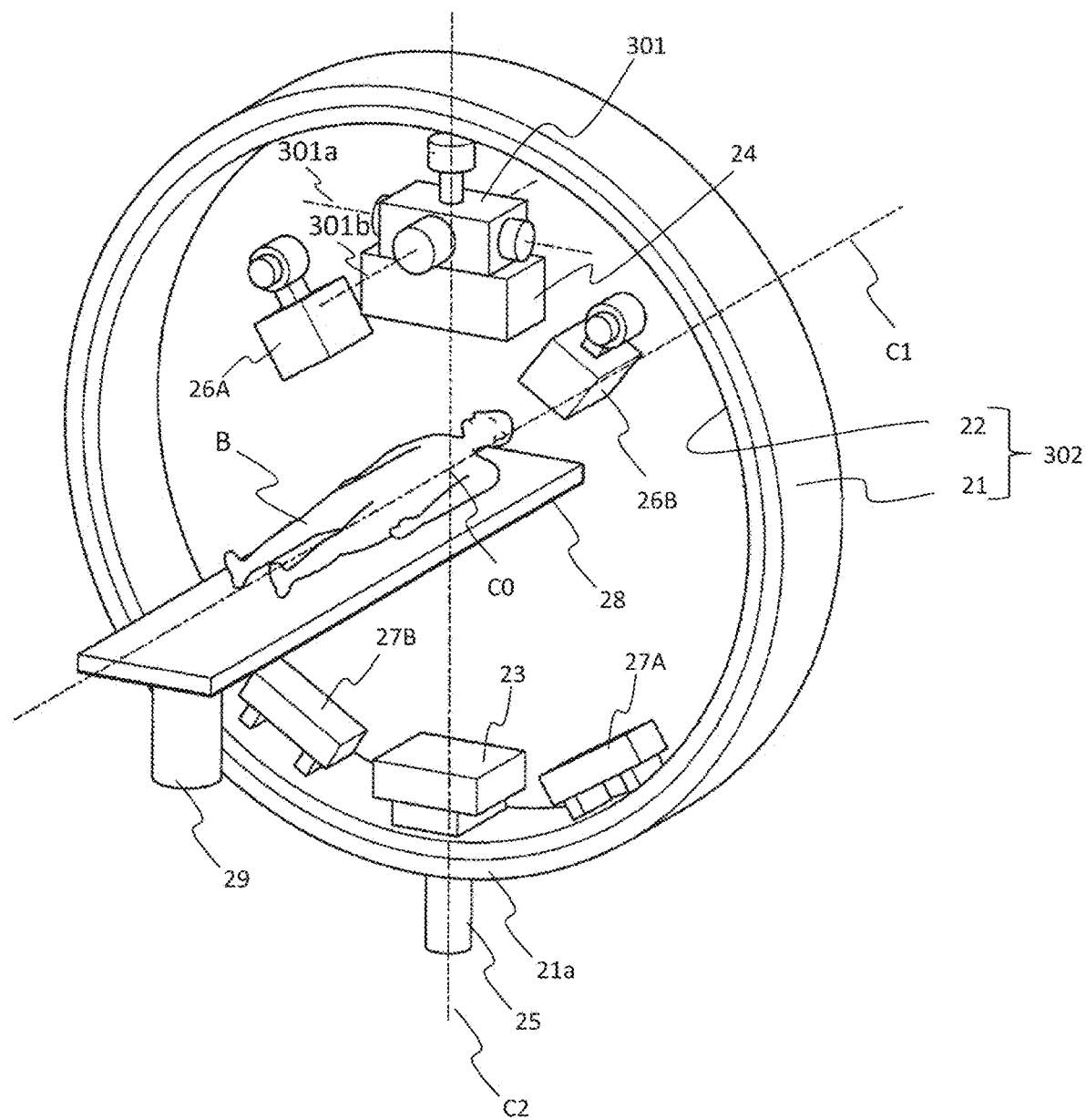
FIG. 2 is a perspective view of a radiation treatment apparatus of the embodiment.

FIG. 2 is a perspective view showing a schematic configuration of the radiation treatment apparatus 20.

As shown in FIG. 2, the radiation treatment apparatus 20 includes the radiation irradiation apparatus 24, a rotation mechanism 302, a couch 28, and the head swing mechanism 301. The rotation mechanism 302 supports the radiation irradiation apparatus 24 and rotates the radiation irradiation apparatus 24 around an isocenter C0. The couch 28 carries a treatment target site of the patient at the isocenter C0. The head swing mechanism 301 is disposed between the radiation irradiation apparatus 24 and the rotation mechanism 302, and swings the radiation irradiation apparatus 24 to swing an irradiation axis of the radiation emitted from the radiation irradiation apparatus 24.

The rotation mechanism 302 includes the ring frame 21 and the rotation ring 22.

The ring frame 21 is disposed such that a rotation central axis C1 faces a substantially horizontal direction. The rotation ring 22 has a structure in which an outer peripheral surface thereof is supported by an inner peripheral surface of the ring frame 21 and the rotation ring 22 can rotate along the inner peripheral surface of the ring frame 21. The rotation ring 22 is driven by a rotation drive mechanism (not shown) and revolves around the rotation central axis C1.

The rotation shaft 25 extending downward is integrally formed on the outer peripheral surface of a lower end portion 21a of the ring frame 21, and the rotation shaft 25 is supported by a base (not shown) in a state in which the ring frame 21 can revolve (pivot) around a vertical central axis (pivot axis) C2 thereof. A pivot drive mechanism (not shown) pivots the ring frame 21 around the pivot axis C2.

Figure 3:
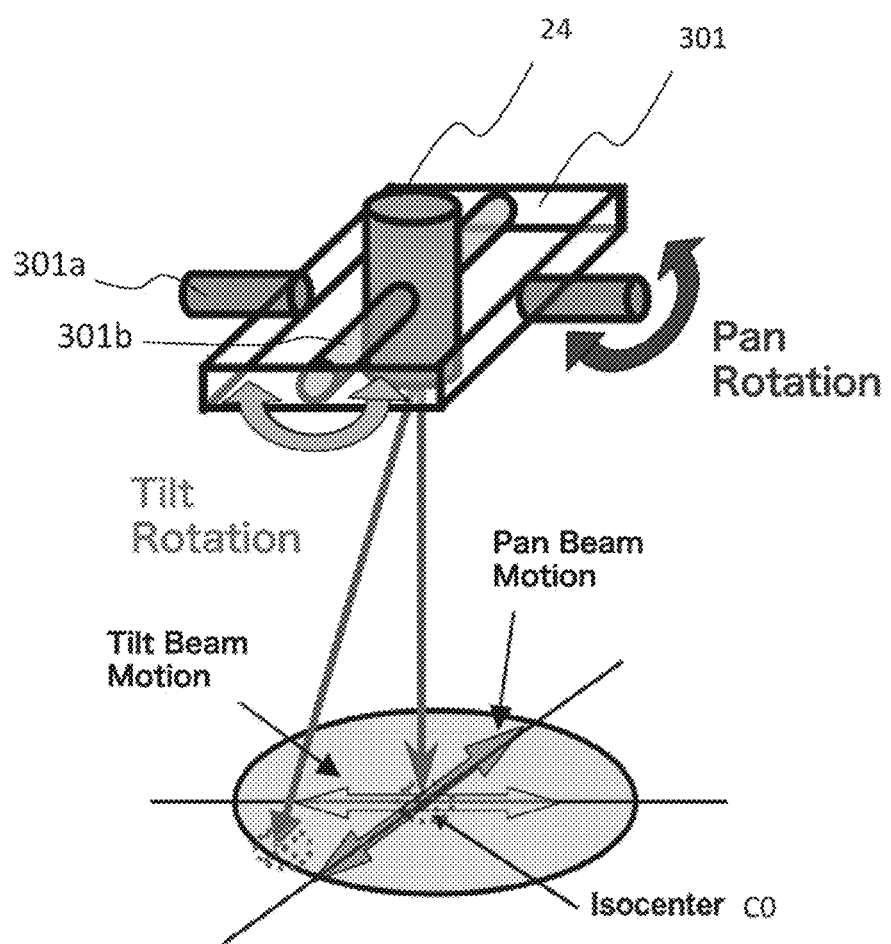
FIG. 3 is a diagram showing a schematic configuration of a head swing mechanism in the radiation treatment apparatus of FIG. 2.

As shown in FIG. 3, the radiation irradiation apparatus 24 is mounted on the head swing mechanism 301 having a gimbal structure, and is supported by the rotation ring 22 via the head swing mechanism 301.

When the head swing mechanism 301 does not operate, radiation Sr emitted from the radiation irradiation apparatus 24 is adjusted to pass through the isocenter C0, which is an intersection of the rotation central axis C1 of the rotation ring 22 and the pivot axis C2 of the ring frame 21.

The radiation treatment apparatus 20 further includes a sensor array 23. The sensor array 23 receives the radiation that is emitted by the radiation irradiation apparatus 24 and that is transmitted through a subject around the isocenter C0 to generate a transmitted image of the subject. As the sensor array 23, an electronic portal imaging device (EPID), a flat panel detector (FPD), an X-ray image intensifier (II), or the like can be used.

Further, the radiation treatment apparatus 20 includes imaging x-ray sources 26A and 26B and sensor arrays 27A and 27B. The imaging X-ray sources 26A and 26B and the sensor arrays 27A and 27B are disposed on an inner peripheral side of the rotation ring 22 and supported by the rotation ring 22. The imaging X-ray sources 26A and 26B are directed to emit imaging X-rays 101 toward the isocenter C0. The imaging X-rays 101 are a conical cone beam. The sensor arrays 27A and 27B are disposed at positions facing the imaging X-ray sources 26A and 26B with the isocenter C0 interposed therebetween, and receive the imaging X-rays 101 that are emitted from the imaging X-ray sources 26A and 26B and that are transmitted through the subject around the isocenter C0 to generate the transmitted image of the subject. As the sensor arrays 27A and 27B, for example, the FPD, the X-ray II, or the like can be used.

A couch drive apparatus 29 can be controlled by the control apparatus 12 to move the couch 28 in parallel with at least the rotation central axis C1.

The head swing mechanism 301 has the gimbal structure equipped with the radiation irradiation apparatus 24, and can tilt the radiation irradiation apparatus 24 around two shafts including a pan shaft 301a and a tilt shaft 301b. The pan shaft 301a is a shaft perpendicular to both the rotation central axis C1 and the pivot axis C2. The tilt shaft 301b is a shaft parallel to the rotation central axis C1.

Figure 4:
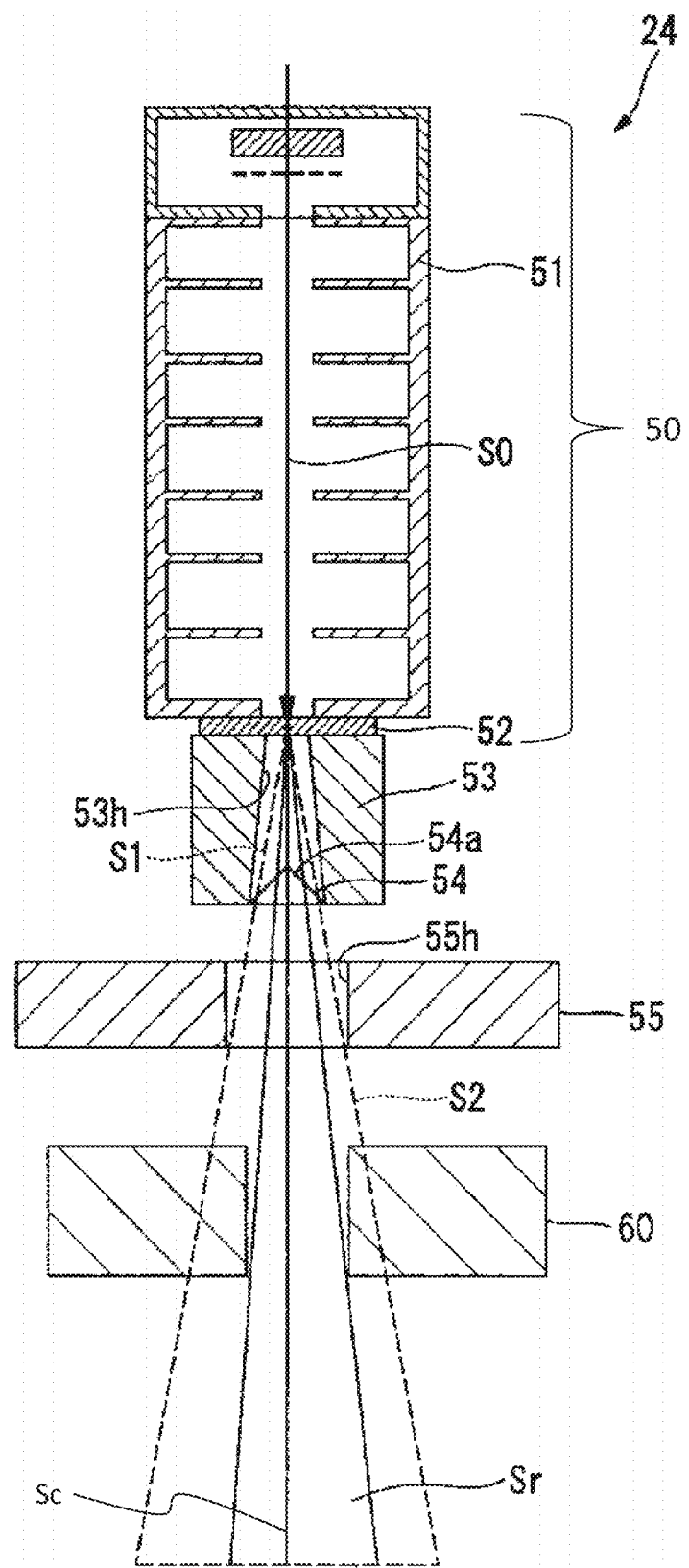
FIG. 4 is a cross-sectional view of a radiation irradiation apparatus of FIG. 3.

As shown in FIG. 4, the radiation irradiation apparatus 24 includes a radiation source 50, a primary collimator 53, a flattening filter 54, a secondary collimator 55, and a multi-leaf collimator (MLC) 60.

Here, the radiation source 50 is an X-ray source including an electron beam accelerator 51 and an X-ray target 52. The electron beam accelerator 51 irradiates the X-ray target 52 with an electron beam S0 generated by accelerating electrons. The X-ray target 52 is made of tungsten, a tungsten alloy, or the like. The X-ray target 52 emits radiation S1 when irradiated with the electron beam S0.

The primary collimator 53 and the secondary collimator 55 are implemented by X-ray shields (lead, tungsten, or the like) including through holes 53h and 55h, respectively, shield a part of the radiation S1, and emit the radiation S1 passing through the through holes 53h and 55h.

The flattening filter 54 includes a conical protrusion 54a made of aluminum or the like, and is disposed on an outlet side of the through hole 53h of the primary collimator 53. The flattening filter 54 makes a dose distribution of the radiation S1 uniform in a plane perpendicular to a radiation direction of the radiation S1.

After passing through the primary collimator 53, the flattening filter 54, and the secondary collimator 55, radiation S2 having a uniform intensity distribution is incident on the multi-leaf collimator 60. The multi-leaf collimator 60 is controlled by the control apparatus 12 to limit an irradiation field of the radiation S2.

Figure 7:
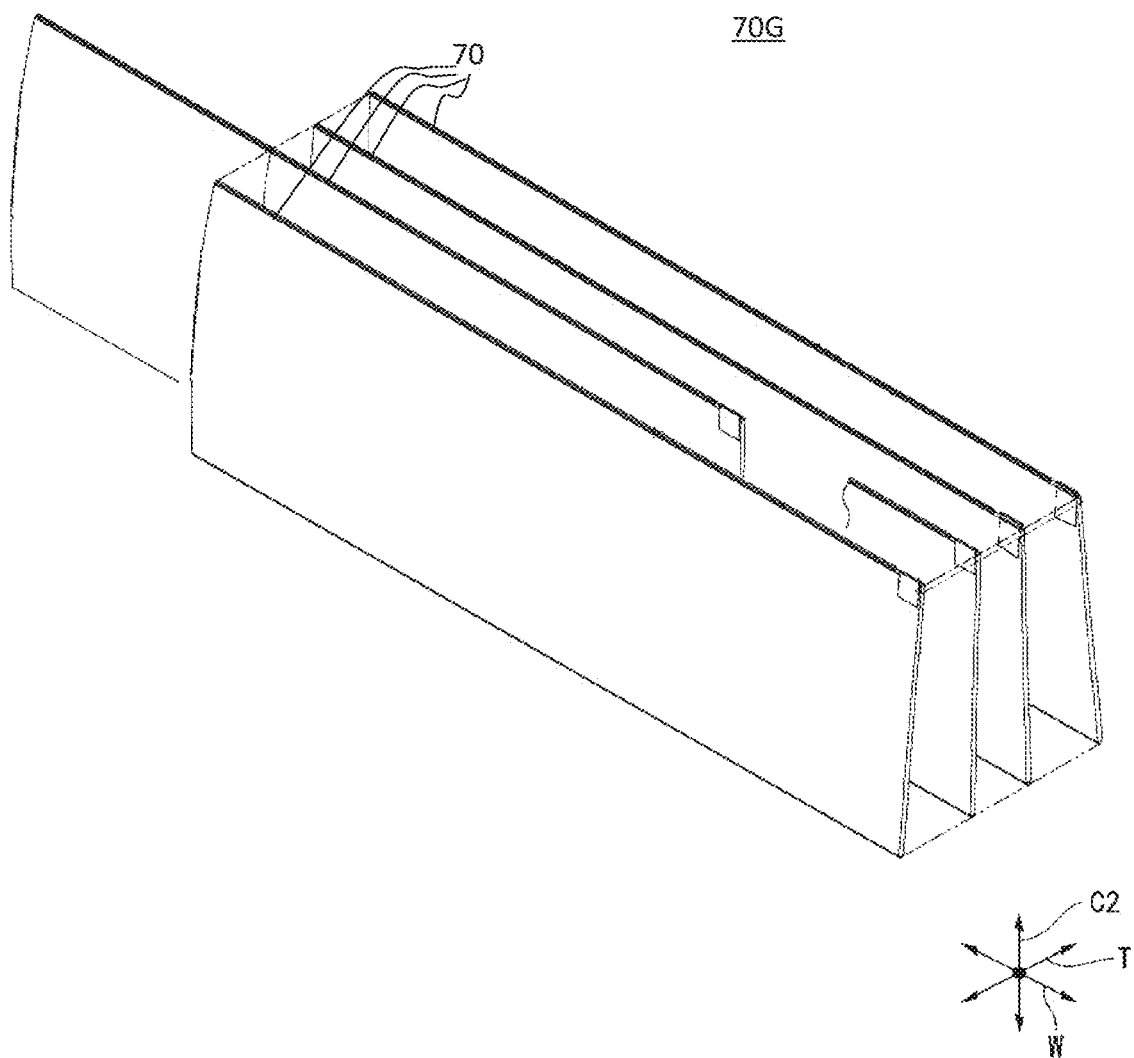
FIG. 7 is a perspective view showing a configuration example of a leaf group of a multi-leaf collimator of FIG. 4.

As shown in FIG. 7, the multi-leaf collimator 60 has a structure in which two sets of leaf groups 70G, in which a plurality of leaves (thin plates) 70 made of a material (lead, tungsten, or the like) that shields the radiation, are arranged in a thickness direction, face each other, and a main plane of the leaves 70 is disposed substantially parallel to the irradiation axis of the radiation. Under control of the control apparatus 12, a drive unit causes each leaf to protrude or retract in a direction that shields the irradiation axis of the radiation, and thus the irradiation field of the radiation S2 can be limited or the dose distribution of the radiation in the irradiation field can be modulated.

Operation of Radiation treatment System

Hereinafter, in the radiation treatment system of the present embodiment, when the patient is irradiated with the radiation to perform a treatment, an operation of the treatment in an irradiation range expansion mode will be described.

In the irradiation range expansion mode, the control apparatus 12 holds an irradiation axis Sc of the radiation in a state of being shifted by a predetermined amount in a predetermined direction from the isocenter C0 by the head swing mechanism 301, and rotates the radiation source 50 (the radiation irradiation apparatus 24) by the rotation mechanism 302 while emitting the radiation from the radiation source with the state of the head swing mechanism maintained.

Figure 5:
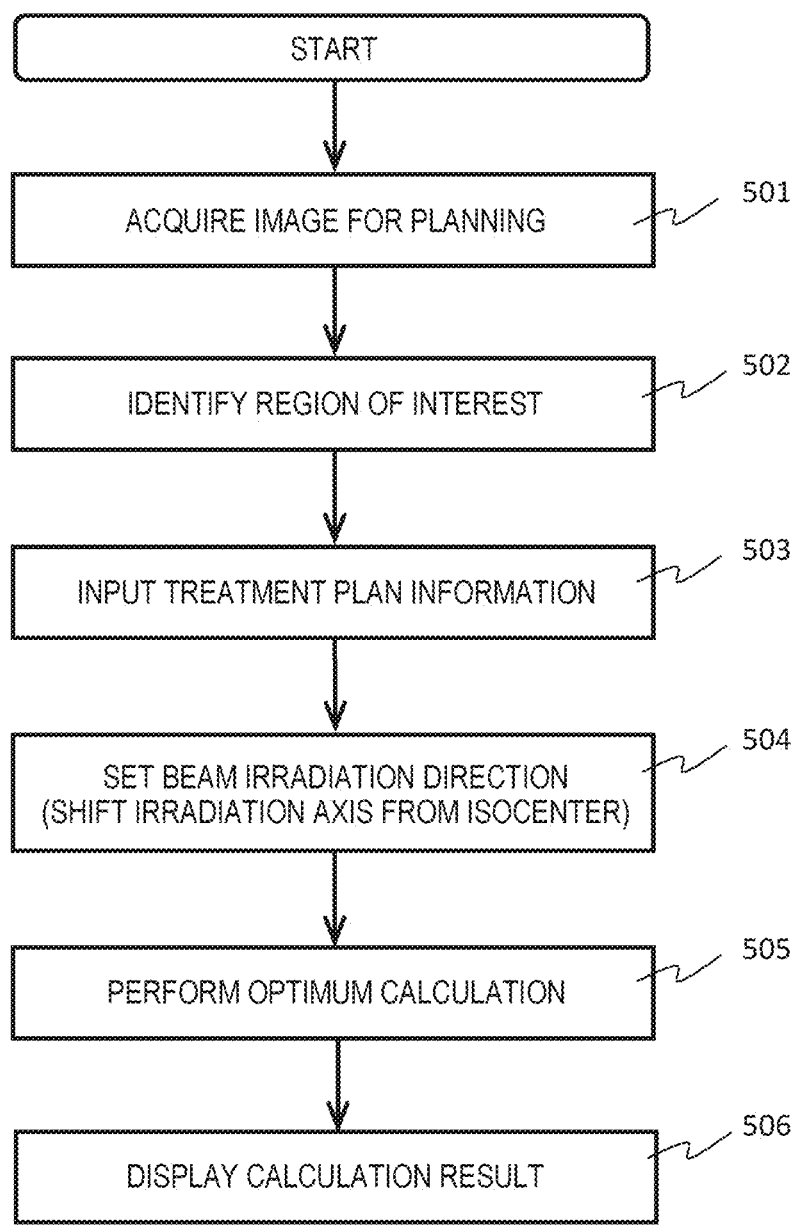
FIG. 5 is a flowchart showing an operation of the radiation treatment system of the embodiment.

First, as shown in a flow of FIG. 5, the treatment planning apparatus 11 acquires the three-dimensional image data for the treatment plan captured in advance for the patient B (step 501). The treatment planning apparatus 11 sets a region of interest such as a region to be irradiated with the radiation or a region to be avoided by extracting a region from the three-dimensional image by image processing, or receiving identification of the region from a user (step 502). Next, the treatment planning apparatus 11 receives information necessary for the treatment plan such as the dose of the radiation to be emitted to each region of interest and an allowable maximum radiation dose from the user (step 503), and creates the dose, the time, the angle, the position, the radiation region, and the like of the radiation to be radiated to the patient B as the treatment plan (step 504). Further, an optimization calculation that takes into consideration a radiation dose rate of the radiation treatment apparatus or an operating range of each machine operating axis is performed, and an optimum intensity distribution of the radiation that can be emitted by the radiation treatment apparatus and that satisfies a radiation dose limit of each region of interest is obtained by the calculation (step 505). For each machine operating axis at this time, each leaf drive axis of the MLC, revolving of the rotation ring 22 around the rotation central axis C1, pivot of the ring frame 21 around the pivot axis C2, and the like are selected and used.

In steps 504 and 505, the treatment planning apparatus 11 determines an amount and a direction of shifting the irradiation axis Sc of the radiation of the radiation source from the isocenter C0 by the head swing mechanism 301, and also calculates a parameter value of a control signal for rotating the radiation source 50 (the radiation irradiation apparatus 24) by the rotation mechanism 302 while emitting the radiation from the radiation source 50 while maintaining the state of the head swing mechanism 301, and a parameter value of the control signal that operates opening and closing of each leaf of the MLC 60 for implementing the optimum intensity distribution of the radiation at that time.

The treatment planning apparatus 11 displays an obtained result of the treatment plan to the user (step 506).

The control apparatus 12 irradiates the patient with the radiation as follows by receiving the parameter value of the control signal calculated to implement the treatment plan by the treatment planning apparatus 11, and controlling the head swing mechanism 301, the rotation angle of the rotation ring 22, and the opening and closing of the leaves of the MLC 60.

Figure 6:
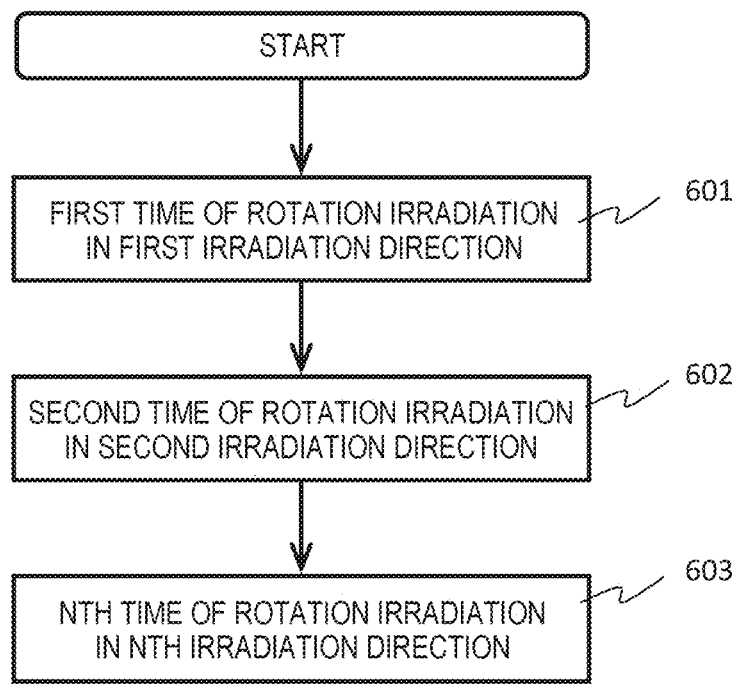
FIG. 6 is a flowchart showing an operation of the radiation treatment system of the embodiment.

Specifically, as in step 601 of a flow of FIG. 6, the control apparatus 12 rotates the pan shaft 301a and/or the tilt shaft 301b of the head swing mechanism 301, sets the irradiation axis Sc of the radiation of the radiation irradiation apparatus 24 to a first irradiation direction 701 shifted by a predetermined amount from the isocenter C0, and, with the state maintained, rotates the radiation source 50 (the radiation irradiation apparatus 24) by the rotation mechanism 302 by a predetermined angle range (here, 360 degrees) while emitting the radiation from the radiation source 50 (step 601). At this time, while the radiation source is rotated, the control apparatus 12 operates the MLC 60 to generate the intensity distribution in a radiation beam. Accordingly, the irradiation of the radiation from the radiation source 50 while rotating the radiation source 50 by the rotation mechanism 302 is referred to as rotation irradiation. That is, step 601 is first rotation irradiation.

Figures 1, 8A:
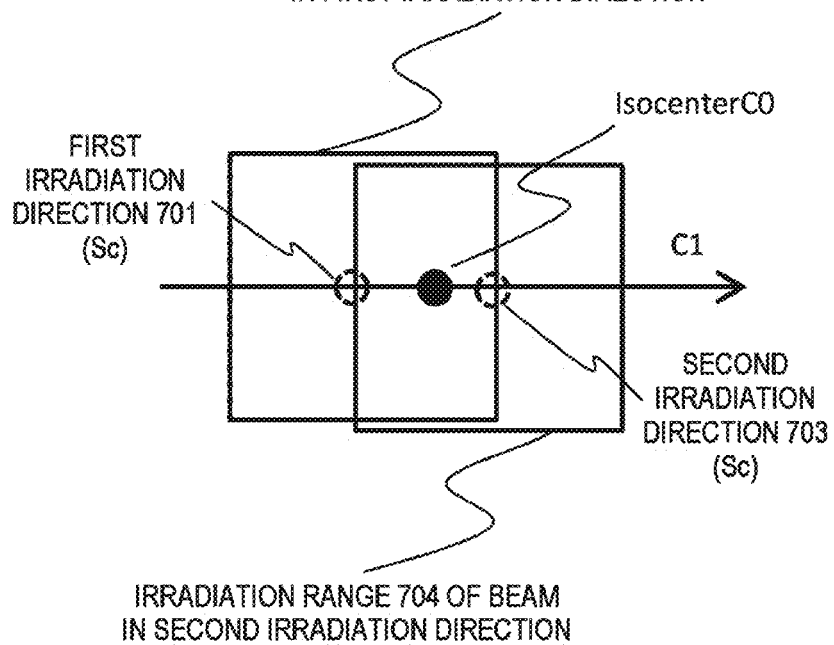
Figures 2, 8A:
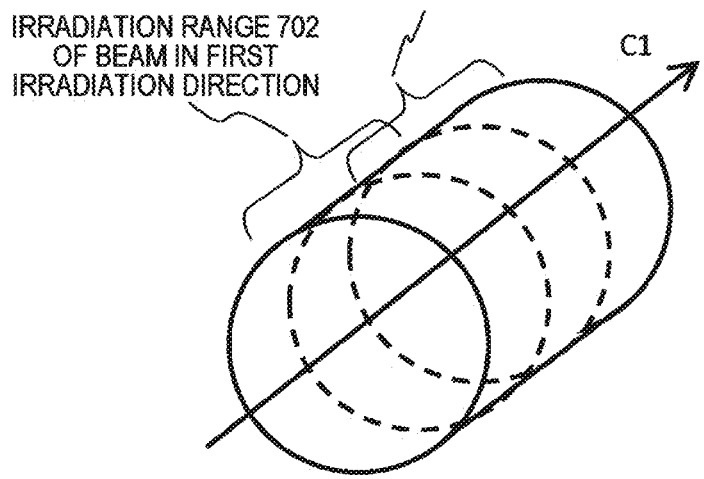
Figures 1, 8B:
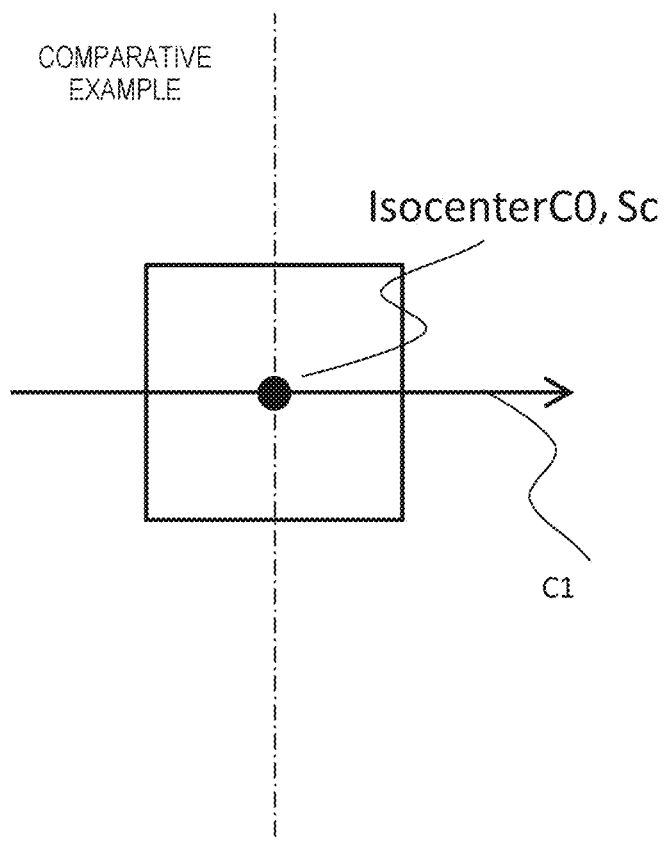
Figures 2, 8B:
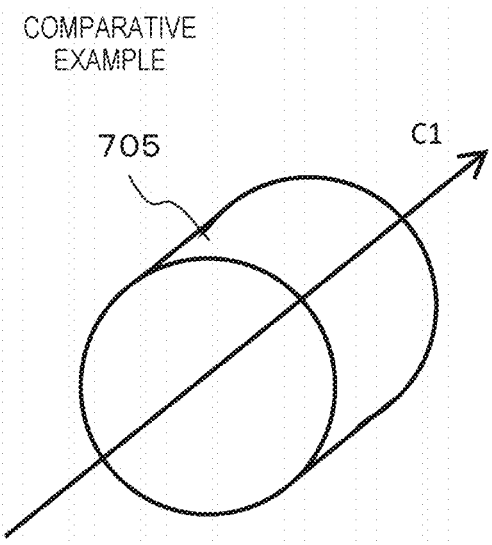

Accordingly, for example, when the first irradiation direction 701 is set on the rotation central axis C1 by the rotation of the pan shaft 301a as shown in FIG. 8A-1, a cylindrical irradiation range 702 is irradiated with the radiation as shown in FIG. 8A-2.

Next, as in step 602, the control apparatus 12 rotates the pan shaft 301a and/or the tilt shaft 301b of the head swing mechanism 301, sets the irradiation axis Sc of the radiation of the radiation irradiation apparatus 24 to a second irradiation direction 703 shifted by a predetermined amount from the isocenter C0, and, with the state maintained, rotates the radiation source 50 (the radiation irradiation apparatus 24) by the rotation mechanism 302 by the predetermined angle range (here, 360 degrees) while emitting the radiation from the radiation source 50 (step 602). At this time, while the radiation source is rotated, the control apparatus 12 operates the MLC 60 to generate the intensity distribution in the radiation beam. Step 602 is second rotation irradiation. At this time, a time of the rotation by the rotation mechanism can be further shortened when the direction is an opposite direction of that of the first rotation irradiation. Alternatively, in a case of a helical scan type, the rotation may be performed in the same direction as that of the first rotation irradiation by setting the irradiation axis Sc to the second irradiation direction 703 while rotating the pan shaft by a pan axis rotation mechanism, for example.

Accordingly, in the first rotation irradiation and the second rotation irradiation, the irradiation axis of the radiation determined by the head swing mechanism 301 is different, and a trajectory of the rotation performed by the rotation mechanism 302 is the same. In the first rotation irradiation and the second rotation irradiation, when the trajectory is the same and the direction is opposite, the rotation is so-called revolving, but in the present specification, the rotation is used as a word including revolving for the sake of convenience.

Accordingly, when the direction of shifting the second irradiation direction 703 as shown in FIG. 8A-1 is set to be an opposite direction of the first irradiation direction 701 (a negative direction of the rotation central axis C1), a cylindrical irradiation range 704 is irradiated with the radiation as shown in FIG. 8A-2.

The processing is repeated N times according to the treatment plan (step 603).

Accordingly, as compared with an irradiation range 705 formed when the radiation source 50 is rotated by the rotation mechanism 302 with the irradiation axis Sc of the radiation directed to the isocenter C0 as in a comparative example, in the present embodiment, the irradiation can be performed in a total range of the irradiation ranges 702 and 704. Therefore, the irradiation range of the radiation can be efficiently widened.

Further, in the above operation of the present embodiment, if the head swing mechanism 301 holding the MLC 60 having a large weight and the radiation source 50 is once directed to the first irradiation direction 701 or the second irradiation direction 703, the rotation may be performed by the rotation mechanism 302 while maintaining the direction, and a burden on the head swing mechanism 301 is small. Therefore, deterioration of irradiation accuracy due to a deflection of the head swing mechanism 301, or the like is unlikely to occur, and the affected part can be irradiated with the radiation with high accuracy.

Further, as shown in FIG. 8A-1, the treatment plan can be set such that the irradiation range 702 of the radiation beam in the first irradiation direction 701 and the irradiation range 704 of the radiation beam in the second irradiation direction 703 (that is, an angular range of a radiation spread angle) include the isocenter C0, respectively. In this case, a range in which the irradiation range 702 and the irradiation range 704 overlap is generated. By generating a desired dose distribution in this overlapping range by the MLC 60, the dose distribution of the total irradiation range of the irradiation ranges 702 and 704 can be designed to a desired distribution.

Figure 9A:
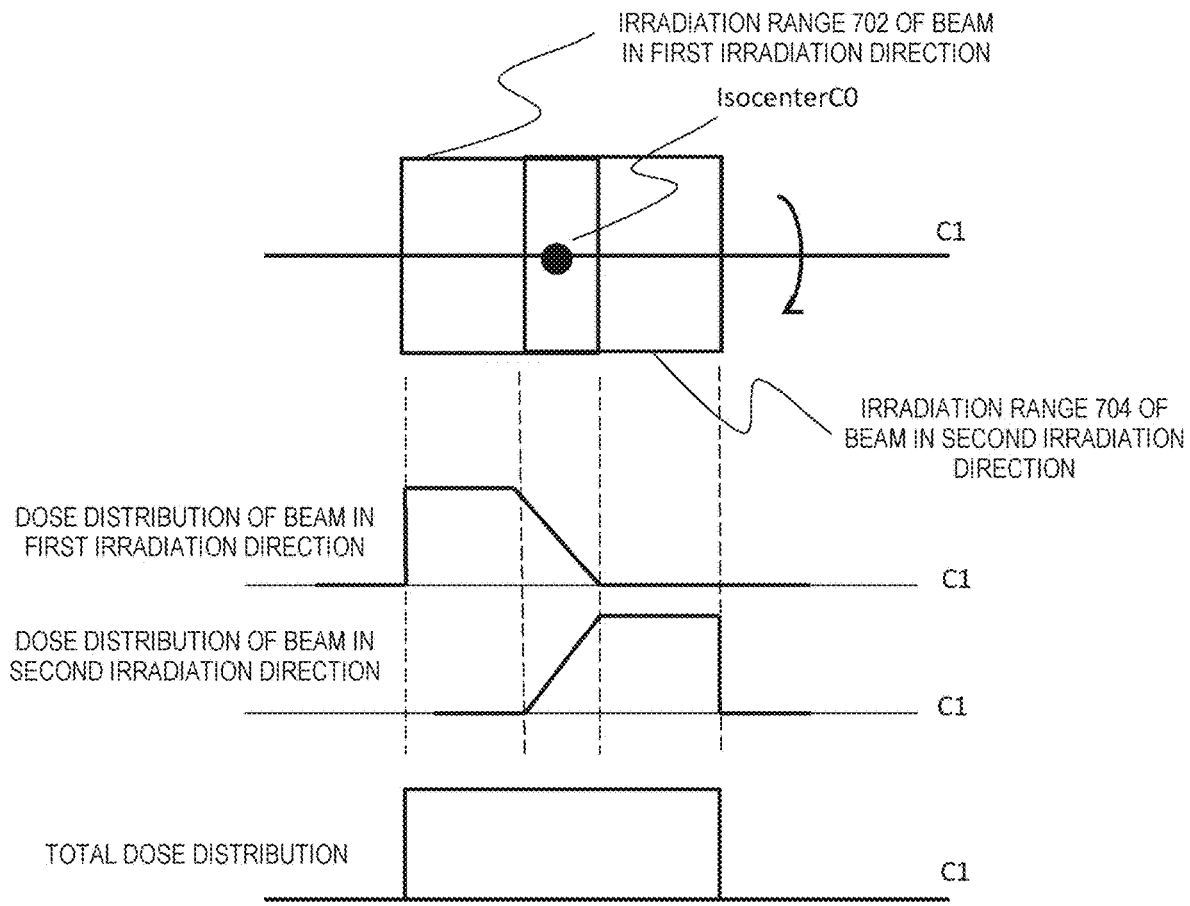
FIG. 9A is a diagram showing dose distributions based on irradiation with beams in the first and second irradiation directions of the radiation irradiation apparatus of the embodiment and a total dose distribution thereof.
Figure 9B:
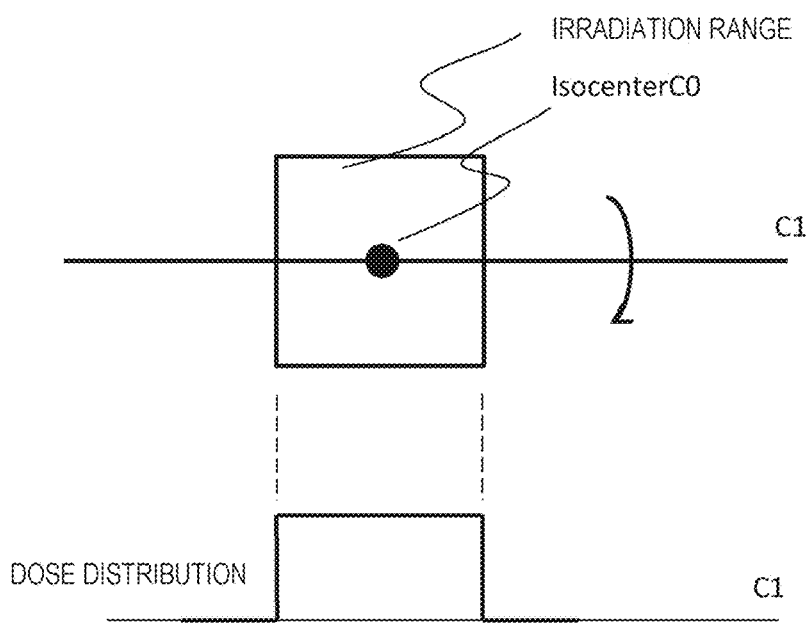
FIG. 9B is a diagram showing a dose distribution based on irradiation with beams of the comparative example.

For example, as shown in FIG. 9A, a total dose distribution in a rotation central axis C1 direction can be flattened by designing the dose distributions in the overlapping range of the irradiation ranges 702 and 704 in a gradual decrease manner and a gradual increase manner in the rotation central axis C1 direction. Accordingly, as in a case where the irradiation axis Sc of the radiation is aligned with the isocenter C0 of the comparative example of FIG. 9B, a flat dose distribution can be obtained as shown in FIG. 9A even in a widened irradiation range.

Further, as shown in FIG. 10, by changing a degree of the gradual decrease and the gradual increase of the dose distributions in the overlapping range of the irradiation ranges 702 and 704 in the rotation central axis C1 direction, a total dose around the isocenter C0 can also be higher than surroundings. Accordingly, it is possible to irradiate a tumor located in the isocenter with a higher dose than the surroundings.

Figure 11:
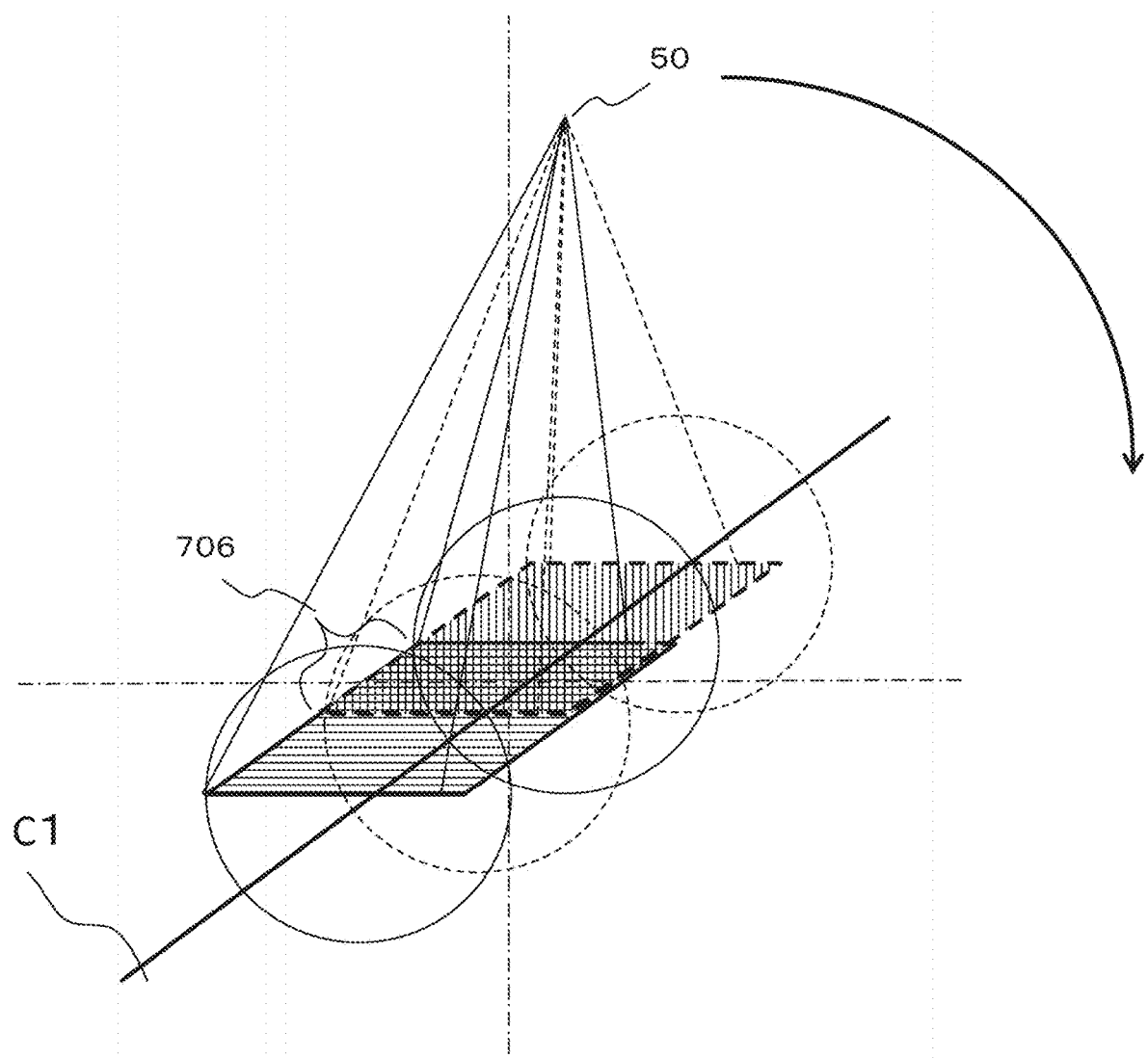
FIG. 11 is a diagram showing an overlap of the irradiation ranges of the radiation irradiation apparatus of the embodiment.

That is, as shown in FIG. 11, a complex dose distribution can be generated in a range 706 where the irradiation ranges 702 and 703 overlap.

Example of Expanding Irradiation Range in Rotation Radial Direction of Rotation Mechanism 302

In FIGS. 8 to 11, an example of expanding the irradiation range in the rotation central axis C1 direction is shown, but in the present embodiment, the irradiation range can also be expanded in a rotation radial direction.

Figure 12:
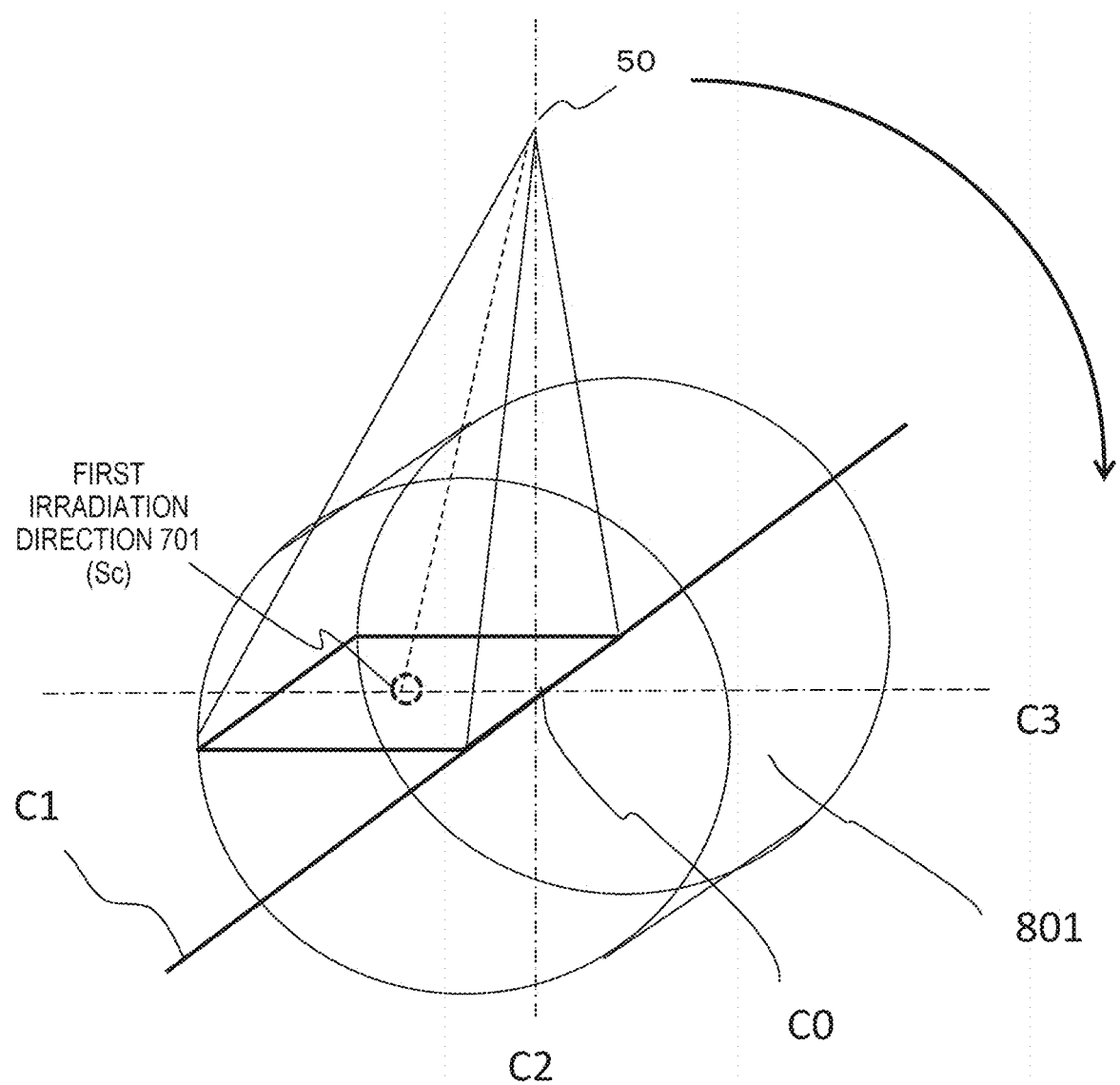
FIG. 12 is a diagram showing an irradiation range when the first irradiation direction of the radiation irradiation apparatus of the embodiment is shifted in a radial direction.

Specifically, as shown in FIG. 12, the control apparatus 12 rotates the tilt shaft 301b of the head swing mechanism 301, shifts the irradiation axis Sc of the radiation in a direction of an axis C3 orthogonal to the rotation central axis C1 and the pivot axis C2, and sets the first irradiation direction 701. With the above state maintained, the radiation source 50 (the radiation irradiation apparatus 24) is rotated by the rotation mechanism 302 by the predetermined angle range (here, 360 degrees) while emitting the radiation from the radiation source 50 (step 601). At this time, while the radiation source is rotated, the control apparatus 12 operates the MLC 60 to generate the intensity distribution in the radiation beam.

Figure 13:
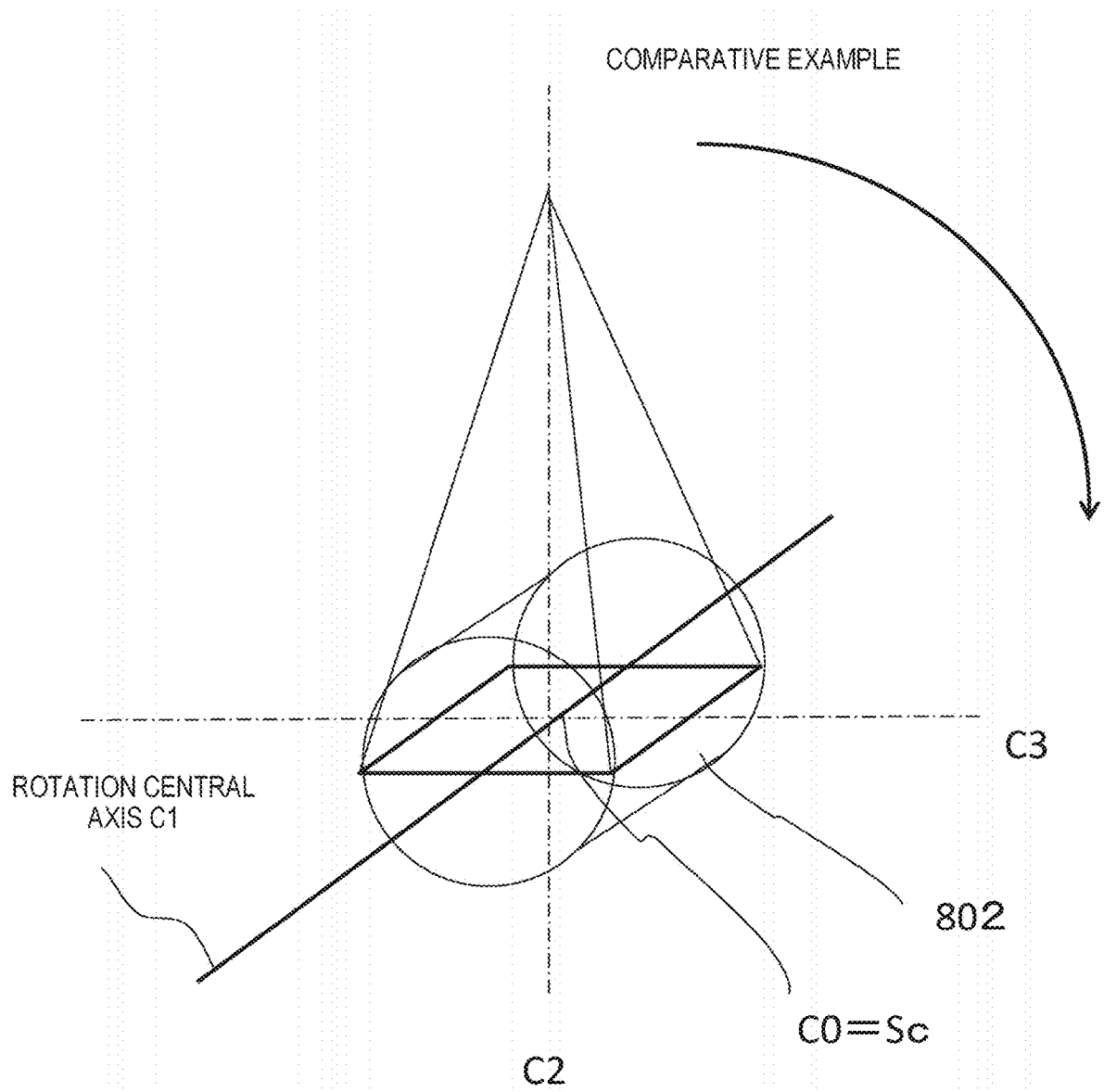
FIG. 13 is a diagram showing the irradiation range of the comparative example.

Accordingly, a cylindrical irradiation range 801 is irradiated with the radiation as shown in FIG. 12. In the irradiation range 801 of FIG. 12, a radius can be expanded to about twice that of an irradiation range 802 in the case where the irradiation axis Sc of the radiation is aligned with the isocenter C0 as shown in FIG. 13 which is the comparative example. In addition, since the burden on the head swing mechanism 301 is small, the deterioration of the irradiation accuracy due to the deflection of the head swing mechanism 301, or the like is unlikely to occur, and the affected part can be irradiated with the radiation with high accuracy.

Example of Expanding Irradiation Range in Rotation Axis Direction and Rotation Radial Direction of Rotation Mechanism 302

Figure 14:
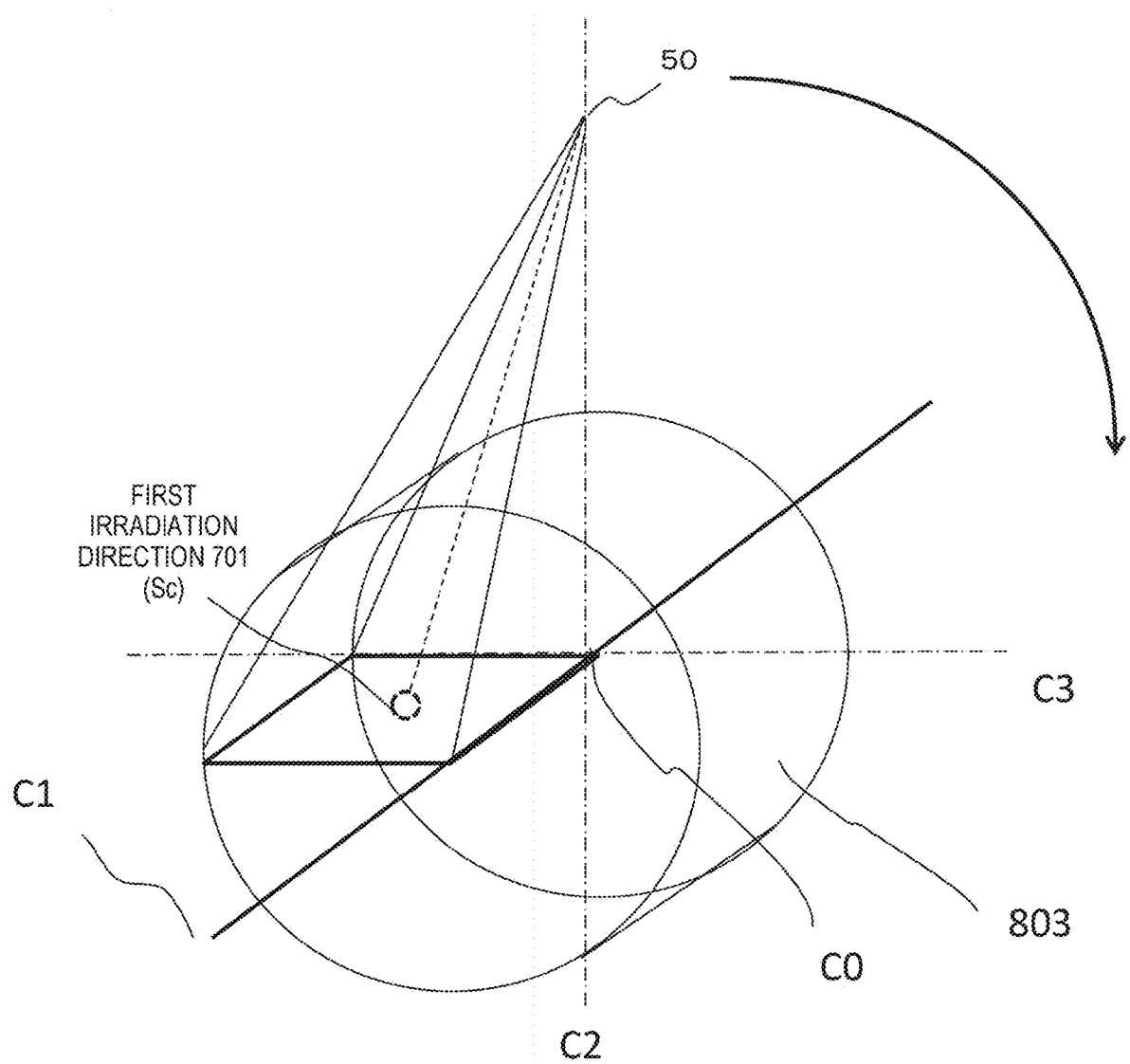
FIG. 14 is a diagram showing an irradiation range when the first irradiation direction of the radiation irradiation apparatus of the embodiment is shifted in the radial direction and a rotation axis direction.

As shown in FIG. 14, the control apparatus 12 may rotate both the pan shaft 301a and the tilt shaft 301b of the head swing mechanism 301, shift the irradiation axis Sc of the radiation in the direction of the rotation central axis C1 and the axis C3, and set the first irradiation direction 701. With the above state maintained, the radiation source 50 (the radiation irradiation apparatus 24) is rotated by the rotation mechanism 302 by the predetermined angle range (here, 360 degrees) while emitting the radiation from the radiation source 50 (step 601). At this time, while the radiation source is rotated, the control apparatus 12 operates the MLC 60 to generate the intensity distribution in the radiation beam.

Accordingly, a cylindrical irradiation range 803 is irradiated with the radiation as shown in FIG. 14. In the irradiation range 803 of FIG. 14, the irradiation range is expanded in the radial direction.

Figure 15:
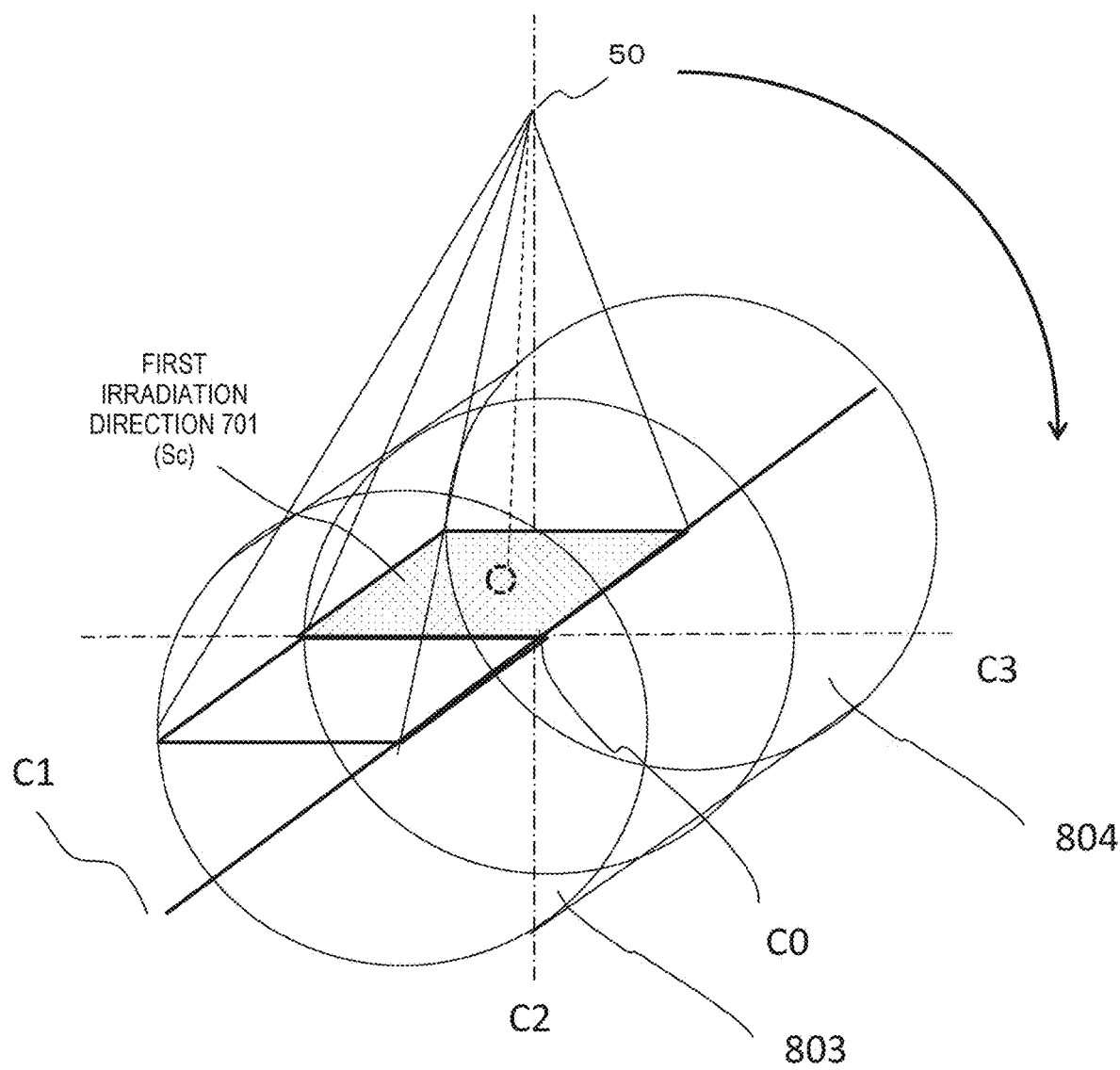
FIG. 15 is a diagram showing an irradiation range when the second irradiation direction of the radiation irradiation apparatus of the embodiment is shifted in the radial direction and the rotation axis direction.

Next, as shown in FIG. 15, the control apparatus 12 rotates both the pan shaft 301a and the tilt shaft 301b of the head swing mechanism 301, shifts the irradiation axis Sc of the radiation in the direction of the rotation central axis C1 and the axis C3, and sets the second irradiation direction 703. In the second irradiation direction 703, the rotation direction of the pan shaft 301a of the head swing mechanism 301 is an opposite direction of that in the case of FIG. 14. With the above state maintained, the radiation source 50 (the radiation irradiation apparatus 24) is rotated by the rotation mechanism 302 by the predetermined angle range (here, 360 degrees) while emitting the radiation from the radiation source 50 (step 602). At this time, while the radiation source is rotated, the control apparatus 12 operates the MLC 60 to generate the intensity distribution in the radiation beam.

Accordingly, as shown in FIG. 15, the cylindrical irradiation range 804 can be expanded about twice in the radial direction and about twice in a length direction.

Figure 16:
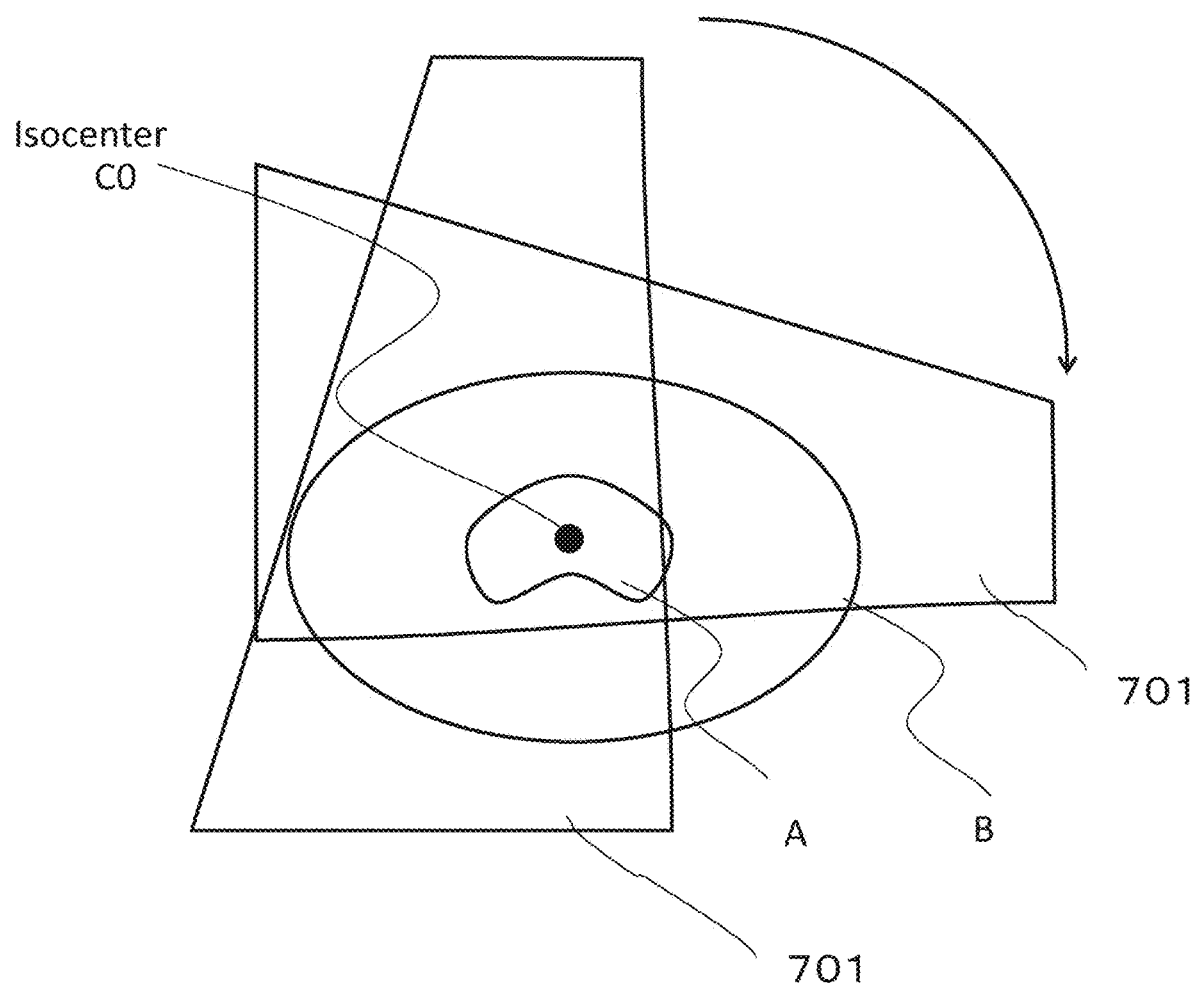
FIG. 16 is a diagram showing that when the irradiation direction is shifted in the radial direction to include an isocenter in the irradiation range of the radiation irradiation apparatus of the embodiment, the dose distribution is larger in a vicinity of the isocenter than in surroundings.

Further, in the examples of FIGS. 12, 14, and 15, the irradiation ranges 702 and 704 shifted by the head swing mechanism 301 do not include the isocenter C0, but as shown in FIG. 16, it is needless to say that the irradiation range 702 can be set to include the isocenter C0. In this case, when the rotation mechanism 302 rotates the radiation source 50 by 360 degrees, the irradiation range 702 is doubled in the isocenter C0 and the vicinity thereof, so that the total dose on a tumor A in the vicinity of the isocenter C0 is larger than that in a surrounding B. Therefore, similar to the total dose distribution shown in FIG. 10, it is possible to irradiate the tumor A located in the isocenter C0 with a higher dose than the surrounding B.

In this case, since the burden on the head swing mechanism 301 is small, the deterioration of the irradiation accuracy due to the deflection of the head swing mechanism 301, or the like is unlikely to occur, and the affected part can be irradiated with the radiation with high accuracy.

Error of Irradiation Amount and Correction Thereof

In a case where the irradiation range 702 of the first rotation irradiation and the irradiation range 704 of the second rotation irradiation are partially overlapped and an entire radiation dose is made uniform, the control apparatus 12 generates the intensity distribution such that the radiation dose with respect to the overlapping portion gradually decreases and gradually increases as described above.

Specifically, the control apparatus 12 operates the MLC 60 at any time during the rotation irradiation, and performs control such that an integrated amount of the radiation emitted to the overlapping portion is a desired value.

However, it is difficult to control the integrated amount of the radiation with high accuracy by the control on the operation of the MLC 60 and the irradiation axis of the head swing mechanism 301, and an error may occur.

Figure 17:
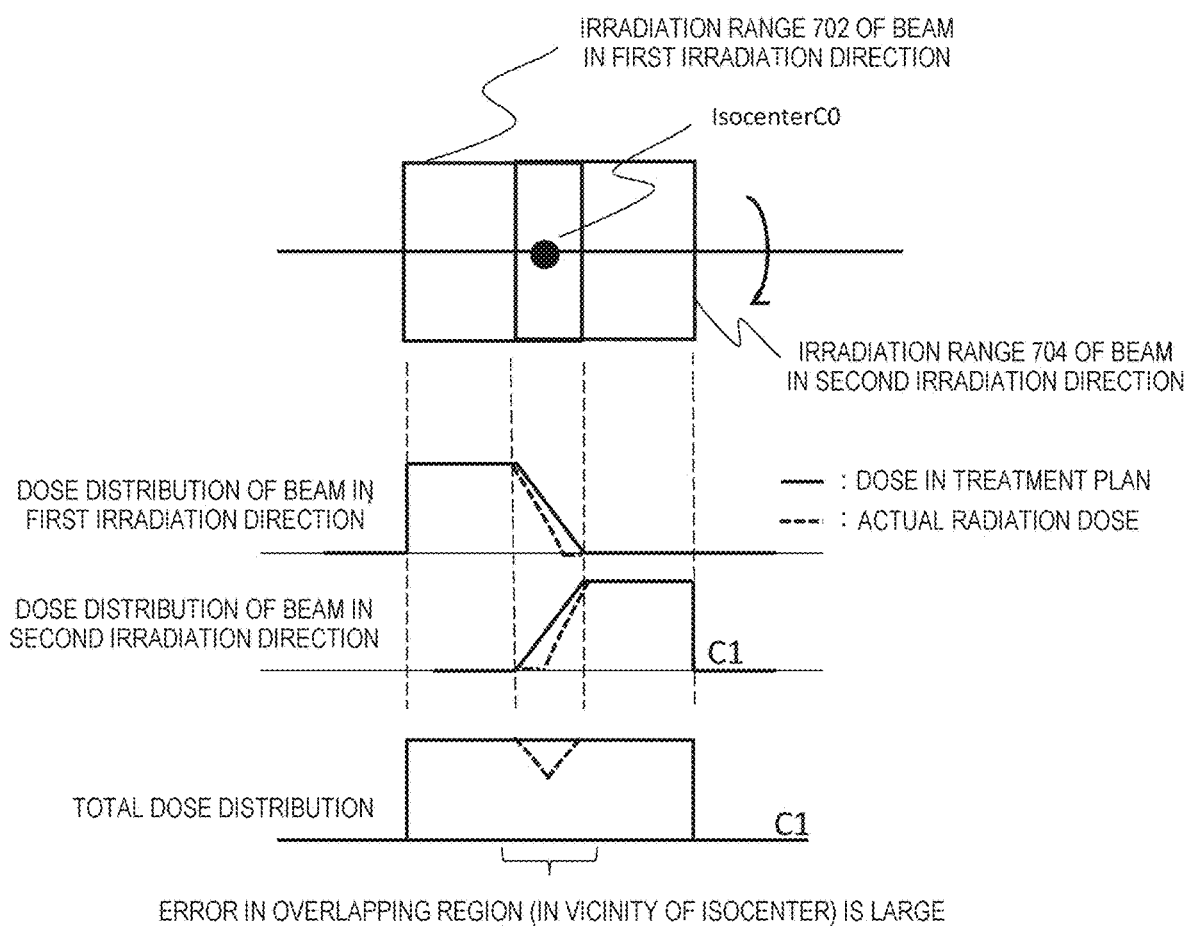
FIG. 17 is a diagram of an error of a radiation dose in an overlapping portion of rotation irradiation.

FIG. 17 is a diagram of the error of the radiation dose in the overlapping portion of the rotation irradiation. In FIG. 17, the dose distribution is controlled such that the radiation dose of the overlapping portion gradually decreases in the first rotation irradiation (beam in the first irradiation direction), and the dose distribution is controlled such that the radiation dose of the overlapping portion gradually increases in the second rotation irradiation (beam in the second irradiation direction).

However, an actual radiation dose is smaller than the dose in the treatment plan in both in the first rotation irradiation and the second rotation irradiation. Therefore, in the total dose distribution, the error is large in the region corresponding to the overlapping portion.

Further, in the example of FIG. 17, since the isocenter is included in an overlapping region and the isocenter is usually expected to be the most accurate, the error in the vicinity of the isocenter may influence the treatment plan.

Therefore, in a case where the irradiation plan in which the irradiation range of the first rotation irradiation and the irradiation range of the second rotation irradiation are partially overlapped is set, the control apparatus 12 acquires the detection result by the sensor array 23 while executing at least the first rotation irradiation, corrects the radiation dose to be emitted to the overlapping portion in subsequent rotation irradiation based on the detection result, and performs the rotation irradiation reflecting the correction. In the present embodiment, the example in which the actual radiation dose is smaller than the dose in the treatment plan in the rotation irradiation is shown, but in the case where the actual radiation dose is larger than the dose in the treatment plan, the correction can also be reflected in the next irradiation plan.

Figure 18:
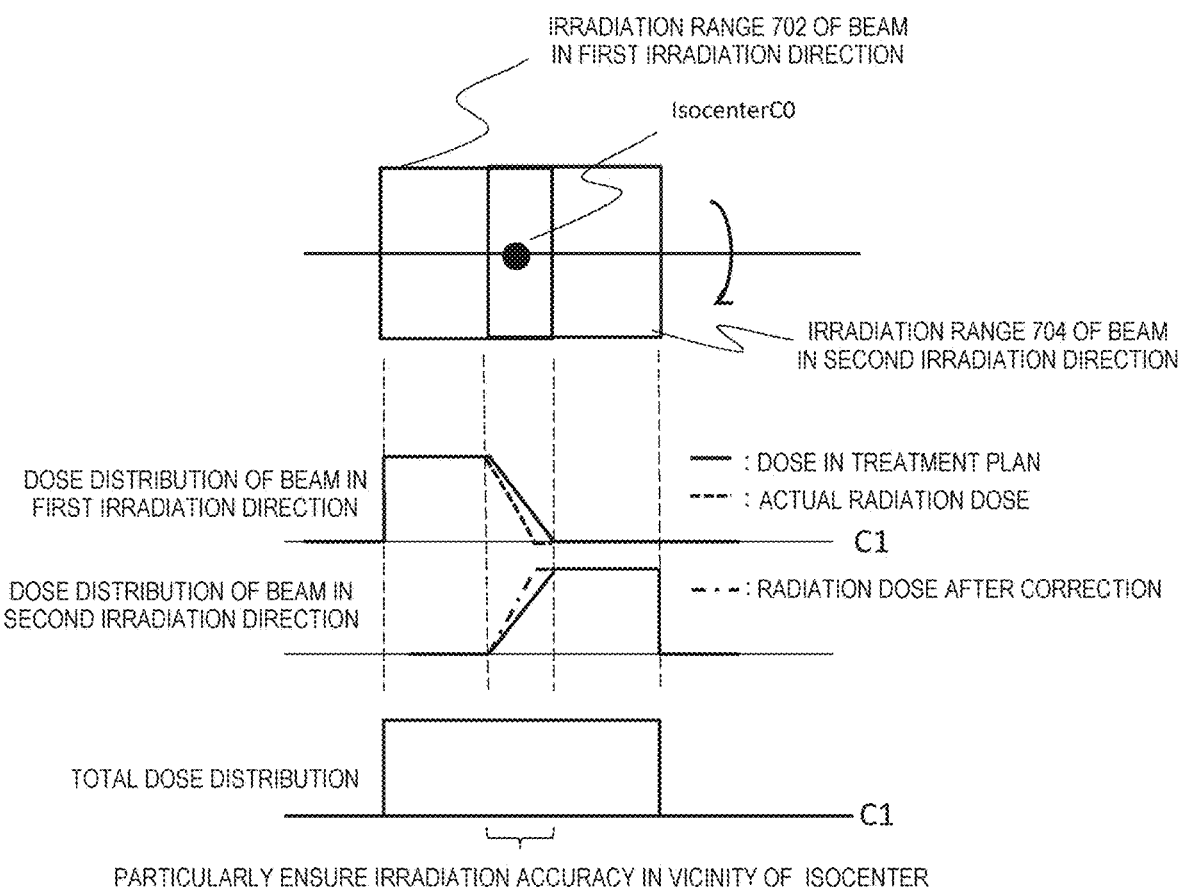
FIG. 18 is a specific example of correction of the radiation dose (No. 1).

FIG. 18 is a specific example of the correction of the radiation dose (No. 1).

In FIG. 18, in the first rotation irradiation (beam in the first irradiation direction), the actual radiation dose is smaller than the dose in the treatment plan.

The control apparatus 12 obtains the actual radiation dose in the first rotation irradiation from the detection result obtained by the sensor array 23, and corrects the radiation dose of the second rotation irradiation (beam in the second irradiation direction) according to the actual radiation dose.

Accordingly, by acquiring the radiation dose of the first rotation irradiation and correcting the second rotation irradiation, the total dose distribution can be made uniform, and in particular, it is possible to ensure the irradiation accuracy in the vicinity of the isocenter.

Figure 19:
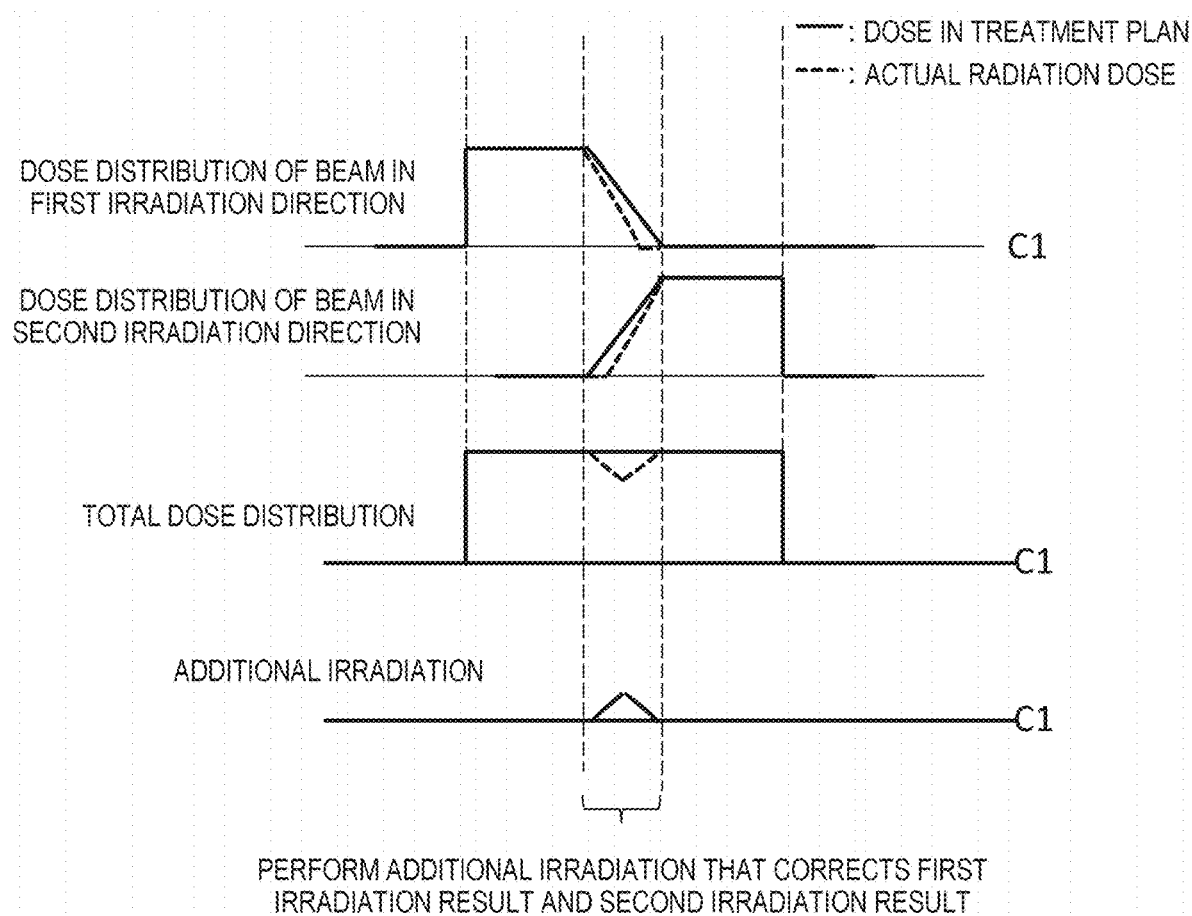
FIG. 19 is a specific example of correction of the radiation dose (No. 2).

FIG. 19 is a specific example of the correction of the radiation dose (No. 2).

In FIG. 19, in both the first rotation irradiation and the second rotation irradiation, the actual radiation dose is smaller than the dose in the treatment plan.

The control apparatus 12 obtains the actual radiation doses in the first rotation irradiation and the second rotation irradiation from the detection result obtained by the sensor array 23, and performs additional rotation irradiation according to the total dose distribution.

Accordingly, by acquiring the radiation doses of the first rotation irradiation and the second rotation irradiation and performing the additional rotation irradiation, the total dose distribution can be corrected and made uniform.

The correction of the second rotation irradiation and the additional irradiation may be executed in combination.

The control apparatus 12 can output the total dose distribution of a plurality of times of the rotation irradiation to the treatment planning apparatus 11, and can reflect the total dose distribution in a next irradiation treatment. Therefore, as a result of the correction of the second rotation irradiation or the additional irradiation, even when the actual radiation dose exceeds the dose in the treatment plan, it is possible to take measures such as reducing the radiation dose in the next irradiation treatment.

Processing such as the creation of the dose distribution in one rotation irradiation, the creation of the total dose distribution, the calculation of the difference between the actual radiation dose and the dose in the treatment plan may be performed with respect to the entire irradiation range, or may be performed selectively for the overlapping portion. A processing load can be reduced by selectively performing the processing on the overlapping portion and reflecting the processing in the subsequent rotation irradiation.

Figure 20:
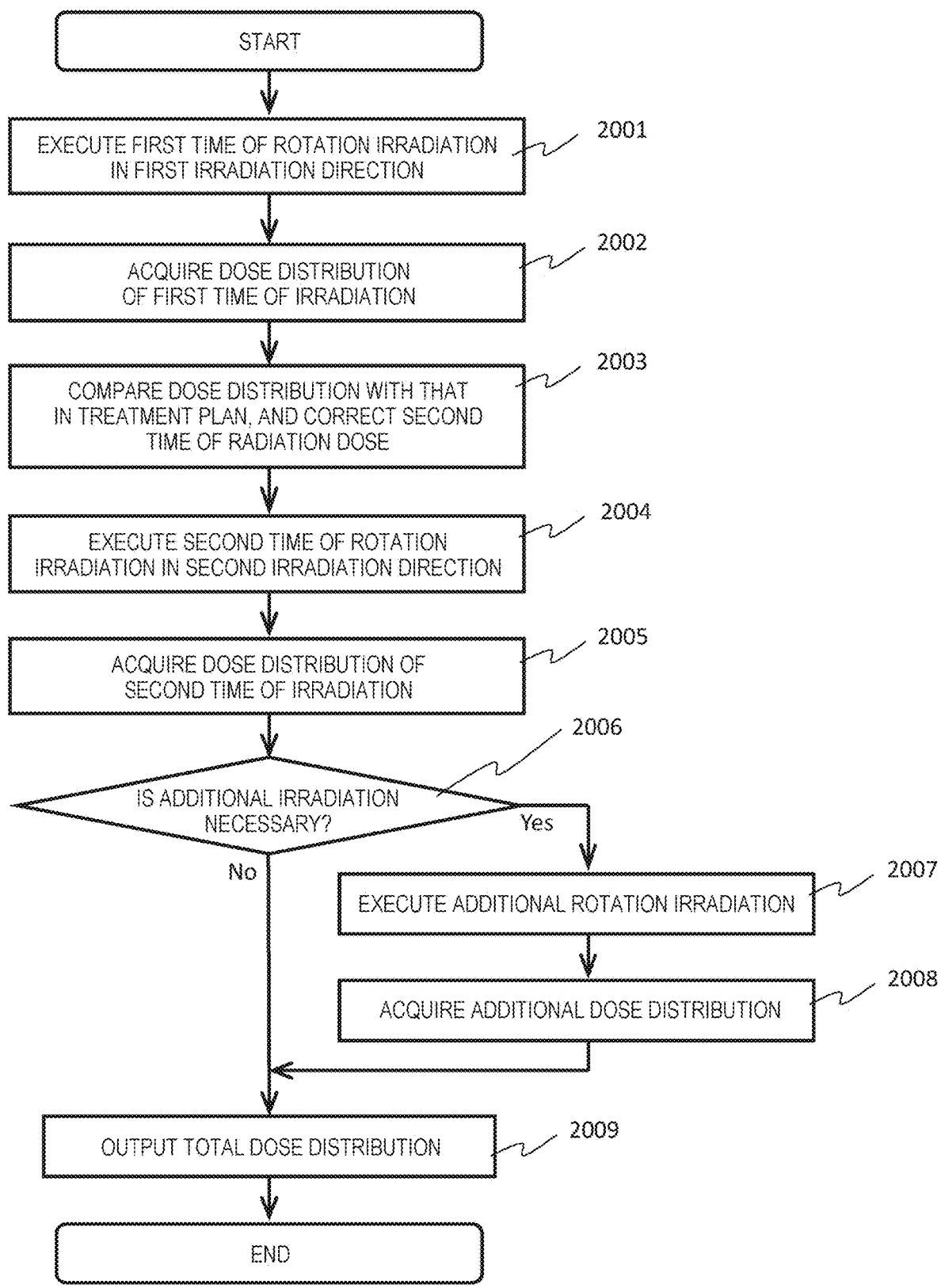
FIG. 20 is a flowchart showing a processing procedure of the correction of the error.

FIG. 20 is a flowchart showing a processing procedure for the correction of the error. In the processing procedure shown in FIG. 20, the control apparatus 12 executes the correction of the second rotation irradiation and the additional irradiation in combination. Specifically, the control apparatus 12 first executes a first time of rotation irradiation (first rotation irradiation) in the first irradiation direction (step 2001). Then, the control apparatus 12 acquires the dose distribution of the first rotation irradiation from the detection result obtained by the sensor array 23 (step 2002).

The control apparatus 12 compares the dose distribution of the first rotation irradiation with that in the treatment plan, and corrects the dose of a second time of the rotation irradiation (second rotation irradiation) (step 2003).

The control apparatus 12 executes the second time of rotation irradiation in the second irradiation direction reflecting the correction (step 2004). Then, the control apparatus 12 acquires the dose distribution of the second rotation irradiation from the detection result obtained by the sensor array 23 (step 2005).

The control apparatus 12 obtains the total dose distribution, compares the total dose distribution with that in the treatment plan, and determines whether the additional irradiation is necessary (step 2006).

If the additional irradiation is necessary (step 2006; Yes), the control apparatus 12 executes the additional rotation irradiation (step 2007), and acquires the dose distribution of the additional rotation irradiation (step 2008). The control apparatus 12 updates the total dose distribution using the acquired additional dose distribution.

After a completion of step 2008, or when the additional irradiation is not necessary (step 2006; No), the control apparatus 12 outputs the total dose distribution (step 2009) and ends the processing.

As a modification, the irradiation may be controlled with reference to a long-term treatment plan.

FIG. 21 is a diagram of irradiation control according to the treatment plan. In FIG. 12, if there is a schedule of the next irradiation treatment within a predetermined number of days, the irradiation control is adopted in which "A second time of radiation dose is corrected based on a first time of dose distribution, and a total of the two doses is adjusted to a target dose.". On the other hand, when there is no schedule of the next irradiation treatment within the predetermined number of days, the irradiation control is adopted in which "The first and second times of radiation doses are set to be small, and the radiation doses are adjusted to the target dose in the additional irradiation.".

Accordingly, if the control apparatus 12 adopts the irradiation control according to the treatment plan, the irradiation can be reliably ended with the time required for the two times of rotation irradiation when the excess or deficiency can be corrected in the next irradiation treatment, and careful irradiation can be performed on a premise of the additional irradiation when the excess or deficiency cannot be expected to be corrected in the next irradiation treatment.

In the above description, the case where the irradiation range is widened by partially overlapping the irradiation ranges of the two times of rotation irradiation has been described as an example, but the irradiation range can be further widened by using three or more times of the rotation irradiation.

Figure 22:
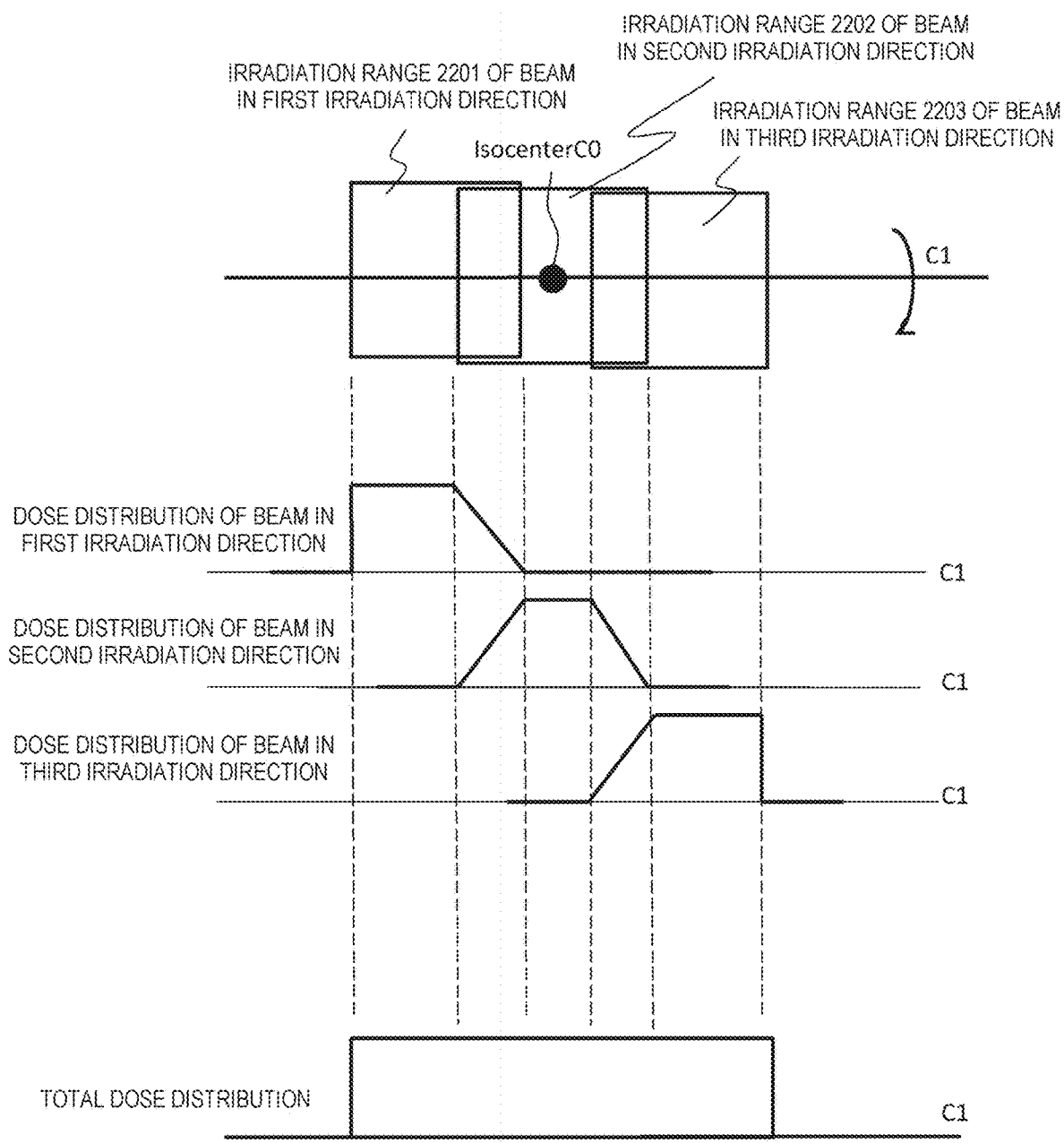
FIG. 22 is a diagram illustrating widening of the irradiation range using three times of the rotation irradiation.

FIG. 22 is a diagram showing widening of the irradiation range using three times of the rotation irradiation.

In FIG. 22, an irradiation range 2202 (of the second rotation irradiation) of the beam in the second irradiation direction includes the isocenter C0 in the vicinity of a center. Then, an irradiation range 2201 (of the first rotation irradiation) of the beam in the first irradiation direction partially overlaps with the irradiation range 2202. Further, an irradiation range 2203 (of third rotation irradiation) of the beam in a third irradiation direction is an opposite direction of that of the irradiation range 2201 with the isocenter C0 as a center, and partially overlaps with the irradiation range 2202.

When the first to third rotation irradiation is performed in this manner, the total dose distribution can also be made uniform by controlling the dose distribution in each overlapping portion.

Modification Applied to Non-rotation Irradiation

In the above description, the case where the irradiation ranges of the first rotation irradiation and the second rotation irradiation are partially overlapped has been described as an example, but the invention is not limited thereto. For example, first irradiation and second irradiation may be performed in which the irradiation ranges are partially overlapped by fixing the rotation mechanism 302 and controlling the head swing mechanism 301.

Accordingly, as well in non-rotation irradiation, which is the irradiation with the rotation mechanism 302 fixed, the detection result obtained by the sensor array 23 can be acquired, and the radiation dose emitted to the overlapping portion in subsequent irradiation can be corrected based on the detection result.

In the non-rotation irradiation, the radiation dose can also be adjusted by operating the multi-leaf collimator 60 during irradiation. Specifically, by gradually moving the leaves for the overlapping portion, the gradual decrease and the gradual increase of the radiation dose are implemented.

In the rotation irradiation, since the head swing mechanism 301 or the like having a weight is rotated by the rotation mechanism 302, a mechanical error of hardware occurs. On the other hand, in the non-rotation irradiation, by performing the irradiation with the rotation mechanism 302 fixed, an error in an entire irradiation amount can be reduced. Further, by using the control of the multi-leaf collimator 60, highly accurate irradiation can be ensured in the overlapping portion where the error is large.

As described above, the disclosed radiation treatment system includes: the couch 28 that carries the treatment target, the radiation source 50, the rotation mechanism 302 that supports the radiation source 50 and that rotates the radiation source 50 around the couch 28, the sensor array 23 as the sensor that detects the radiation transmitted through the treatment target, and the control apparatus 12 as the control unit that controls the radiation source 50 and the rotation mechanism 302, and the control unit sets an irradiation plan in which an irradiation range of first irradiation and an irradiation range of second irradiation are partially overlapped, and controls a radiation dose for an overlapping portion based on a detection result obtained by the sensor.

Therefore, the disclosed radiation treatment system enables wide range irradiation with high accuracy.

According to the disclosed radiation treatment system, the control unit is able to execute rotation irradiation in which the radiation is emitted from the radiation source while rotating the radiation source by the rotation mechanism, and the first irradiation and the second irradiation are the rotation irradiations, respectively.

Therefore, the irradiation range can be expanded by partially overlapping the irradiation ranges in the rotation irradiation, and the radiation dose in the expanded irradiation range can be controlled with high accuracy.

The disclosed radiation treatment system further includes the head swing mechanism 301 that swings the radiation source so as to swing an irradiation axis of the radiation, in the rotation irradiation, the radiation is emitted from the radiation source 50 while rotating the radiation source 50 by the rotation mechanism 302 with the state of the head swing mechanism 301 maintained, and the first irradiation and the second irradiation are the rotation irradiations in which irradiation axes of the radiation are different and trajectories of the rotation performed by the rotation mechanism are the same.

Therefore, it is possible to avoid a situation in which the accuracy of the radiation irradiation is reduced due to operation accuracy of the head swing mechanism 301.

The control unit can acquire an irradiation result of the first irradiation by the sensor and can correct a radiation dose to be emitted to the overlapping portion in the second irradiation.

In addition, the control unit can acquire the irradiation results of the first irradiation and the second irradiation by the sensor, and can perform the additional irradiation when the radiation dose with respect to the overlapping portion is insufficient.

Accordingly, the disclosed radiation treatment system can correct the error in the radiation dose by the correction of the second irradiation or the additional irradiation.

The disclosed radiation treatment system further includes the multi-leaf collimator 60 that partially shields the radiation so as to form a shape of the irradiation range of the radiation, and the control unit controls an integrated amount of the radiation emitted to the overlapping portion by operating the multi-leaf collimator at any time while performing the irradiation from the radiation source.

Therefore, the intensity distribution can be generated in the radiation beam, which contributes to the highly accurate irradiation.

The control unit can selectively obtain a difference between a radiation dose in the irradiation plan and a radiation dose actually emitted to the overlapping portion, and reflect the difference in subsequent irradiation.

According to this control, it is possible to implement the highly accurate irradiation while preventing a load on the calculation.

The control unit can output a total dose distribution obtained based on a plurality of times of irradiation and reflect the total dose distribution in a next irradiation treatment.

The control unit can determine the irradiation plan according to a time until a next irradiation treatment in a treatment plan.

Therefore, an adaptive radiation treatment can be performed in conjunction with the treatment plan.

The invention is not limited to the above disclosed contents, and includes various modifications. For example, the embodiment described above has been described in detail for easy understanding of the invention, and the invention is not necessarily limited to those including all the configurations described above. In addition, the configuration is not limited to being deleted, and the configuration may be replaced or added.

For example, in the above embodiment, the irradiation range of the first rotation irradiation and the irradiation range of the second rotation irradiation are partially overlapped by using the head swing mechanism 301, but the irradiation range of the first rotation irradiation and the irradiation range of the second rotation irradiation may be partially overlapped by moving the couch.

The irradiation range of the first rotation irradiation and the irradiation range of the second rotation irradiation may be partially overlapped by using not only the head swing mechanism 301 but also another mechanism such as a slide mechanism.

What is claimed is:

1. A radiation treatment system comprising:
   a couch that carries a treatment target;
   a radiation source;
   a rotation mechanism configured to support the radiation source and to rotate the radiation source around the couch;
   a sensor configured to detect radiation transmitted through the treatment target; and
   a control unit configured to control the radiation source and the rotation mechanism,
   a head swing mechanism configured to swing the radiation source so as to swing an irradiation axis of the radiation; and
   a multi-leaf collimator configured to partially shield the radiation so as to form a shape of an irradiation range of the radiation,
   wherein the control unit is configured to execute rotation irradiation in which the radiation is emitted from the radiation source while the radiation source is rotated by the rotation mechanism,
   wherein a first irradiation and a second irradiation are the rotation irradiation in which irradiation axes of the radiation are different and trajectories of the rotation performed by the rotation mechanism are the same, wherein the control unit is configured to:
set an irradiation plan in which an irradiation range of the first irradiation and an irradiation range of the second irradiation partially overlap,
control an integrated amount of the radiation emitted to the overlapping portion by causing the multi-leaf collimator to operate at any time while performing the irradiation from the radiation source, and
selectively obtain a difference between a radiation dose in the irradiation plan and a radiation dose actually emitted to the overlapping portion based on a detection result obtained by the sensor and reflect the difference in a subsequent irradiation.

2. The radiation treatment system according to claim 1, wherein in the rotation irradiation, the radiation is emitted from the radiation source while rotating the radiation source by the rotation mechanism with a state of the head swing mechanism maintained.

3. The radiation treatment system according to claim 1, wherein the control unit is configured to acquire an irradiation result of the first irradiation by the sensor and corrects the radiation dose emitted to the overlapped portion in the second irradiation.

4. The radiation treatment system according to claim 1, wherein the control unit is configured to acquire irradiation results of the first irradiation and the second irradiation by the sensor, and perform additional irradiation when the radiation dose with respect to the overlapped portion is insufficient.

5. The radiation treatment system according to claim 1, wherein the control unit is configured to outputs a total dose distribution obtained based on a plurality of times of irradiation and reflects the total dose distribution in a next irradiation treatment.

6. The radiation treatment system according to claim 1, wherein the control unit is configured to determine the irradiation plan according to a time until a next irradiation treatment in a treatment plan.

7. A method of operating a radiation treatment system including:
a couch that carries a treatment target,
a radiation source,
a rotation mechanism configured to support the radiation source and to rotate the radiation source around the couch,
a sensor configured to detect radiation transmitted through the treatment target,
a head swing mechanism configured to swing the radiation source so as to swing an irradiation axis of the radiation,
a multi-leaf collimator configured to partially shield the radiation so as to form a shape of an irradiation range of the radiation,
a control unit configured to control the radiation source and the rotation mechanism, the method comprising steps executed by the control unit:
executing rotation irradiation in which the radiation is emitted from the radiation source while the radiation source is rotated by the rotation mechanism, wherein a first irradiation and a second irradiation are the rotation irradiation in which irradiation axes of the radiation are different and trajectories of the rotation performed by the rotation mechanism are the same;
setting an irradiation plan in which an irradiation range of the first irradiation and an irradiation range of the second irradiation partially overlap;
controlling an integrated amount of the radiation emitted to the overlapping portion by causing the multi-leaf collimator to operate at any time while performing the irradiation from the radiation source; and
selectively obtaining a difference between a radiation dose in the irradiation plan and a radiation dose actually emitted to the overlapping portion based on a detection result obtained by the sensor and reflect the difference in a subsequent irradiation.

* * * * *